United States Patent
Cheng et al.

(10) Patent No.: US 7,897,340 B2
(45) Date of Patent: Mar. 1, 2011

(54) USE OF TUMOR SUSCEPTIBILTY GENE 101 (TSG 101) AS A PROGNOSTIC AND DIAGNOSTIC MARKER

(75) Inventors: Xiaodong Cheng, League City, TX (US); Fang Mel, League City, TX (US); Travis Young, Galveston, TX (US); Jinsong Liu, Houston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 89 days.

(21) Appl. No.: 11/706,109

(22) Filed: Feb. 13, 2007

(65) Prior Publication Data
US 2007/0243547 A1    Oct. 18, 2007

Related U.S. Application Data

(60) Provisional application No. 60/772,794, filed on Feb. 13, 2006.

(51) Int. Cl.
*C12Q 1/68* (2006.01)
*G01N 33/53* (2006.01)

(52) U.S. Cl. .............................. 435/6; 435/7.1
(58) Field of Classification Search .......................... None
See application file for complete search history.

(56) References Cited

U.S. PATENT DOCUMENTS

| 6,835,816 B2 * | 12/2004 | Cohen et al. ............ 530/387.1 |
| 6,962,779 B1 * | 11/2005 | Macina ......................... 435/6 |
| 2006/0193848 A1 * | 8/2006 | Cohen et al. ............ 424/133.1 |

OTHER PUBLICATIONS

Lin, Chen, and Chang. Multiple truncated transcripts of TSG101 in gastrointestinal cancers. Journal of Gastroenterology and Hepatology, 1998. vol. 13, pp. 1111-1114.*
Perkins, Slater, Sanders, and Prichard. Serum tumor markers. American Family Physician, 2003. vol. 68, pp. 1075-1082.*
Erbagci, Yilmaz, and Kutlar. Menstrual cycle dependent variability for serum tumor markers CEA, AFP, CA 19-9, CA125 and CA15-3 in healthy women. Disease Markers, 1999. vol. 15, pp. 259-267.*
National Cancer Institute. Digestive/Gastrointestinal Cancers. www.cancer.gov/cancertopics/cancersbybodylocation/ Aug. 24, 2009.*
TSG101 gene information, http://www.ihop-net.org/UniPub/iHOP/gs/92891.html as downloaded Apr. 5, 2010. 2 pages.*
Liu, Huang, You, Chou, Hu, Chao, Chen, and Cheng. Overexpression of tumor susceptibility gene TSG101 in human papillary thyroid carcinomas. Oncogene, 2002. vol. 21, pp. 4830-4837.*

* cited by examiner

*Primary Examiner* — Misook Yu
*Assistant Examiner* — Anne M. Gussow
(74) *Attorney, Agent, or Firm* — Benjamin Aaron Adler

(57) ABSTRACT

The present invention discloses the link between oncogenic Ras and TSG101 and the negative effect of TSG101 on the expression of p21 in ovarian cancer. The present also discloses the use of TSG101 as a prognostic, diagnostic marker and a potential therapeutic target in cancer, especially ovarian cancer.

11 Claims, 10 Drawing Sheets

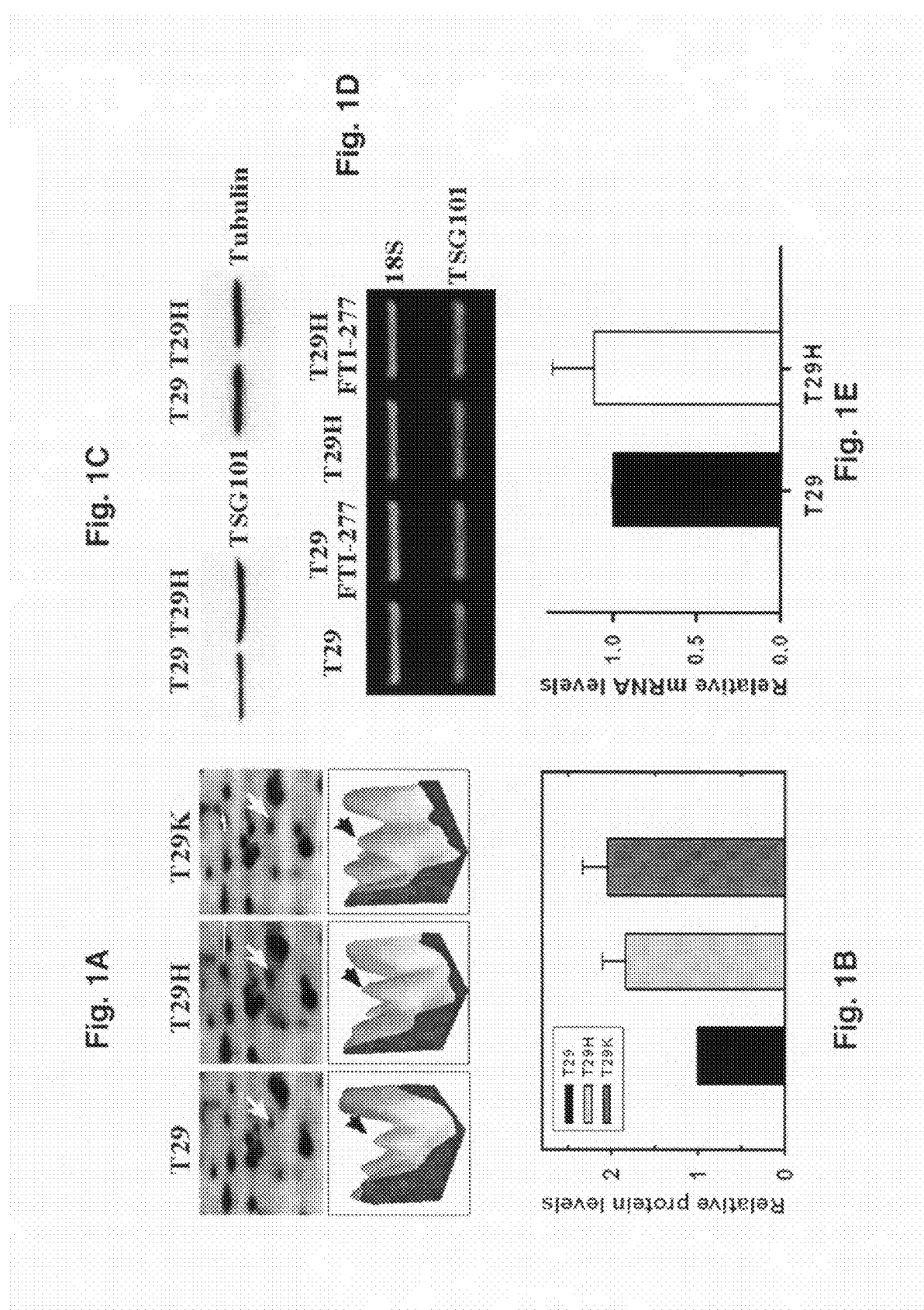

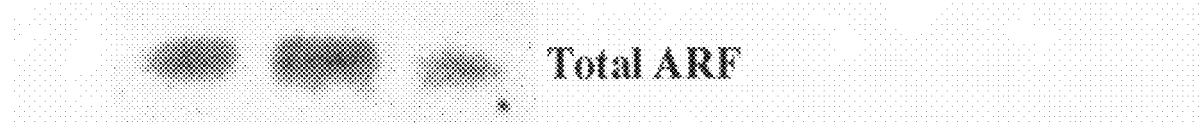
Fig. 3A
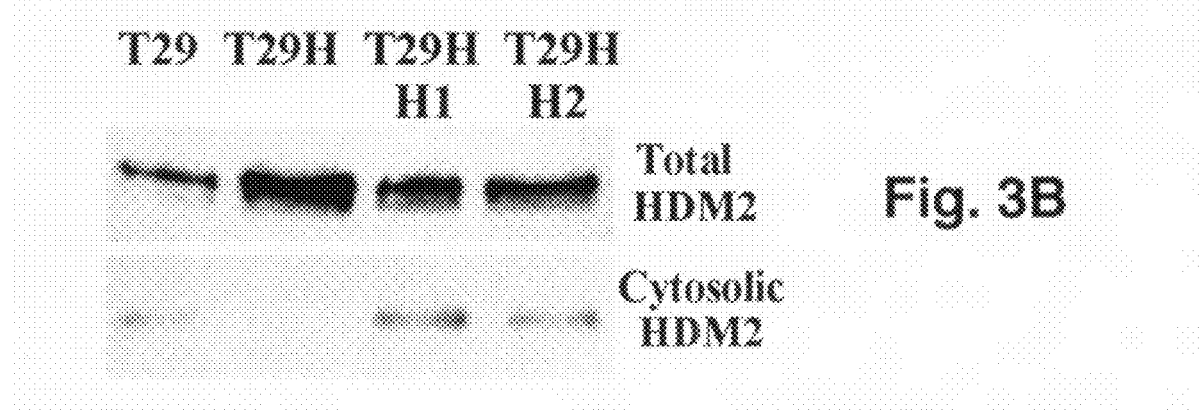
Fig. 3B
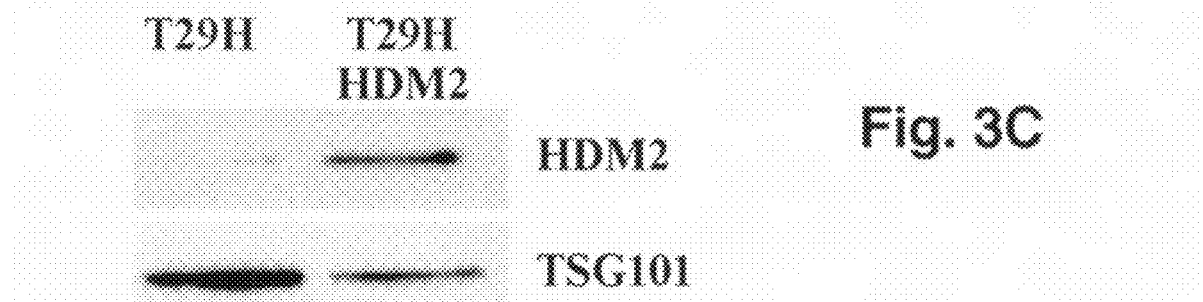
Fig. 3C

Fig. 9A
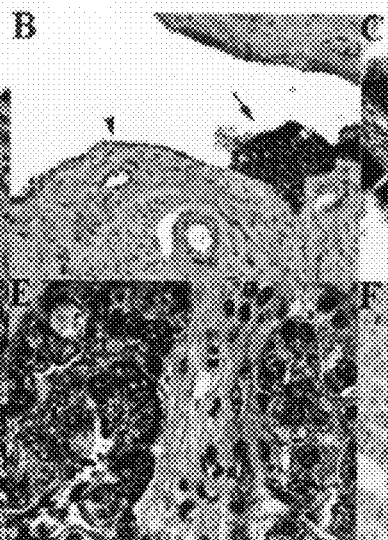
Fig. 9B
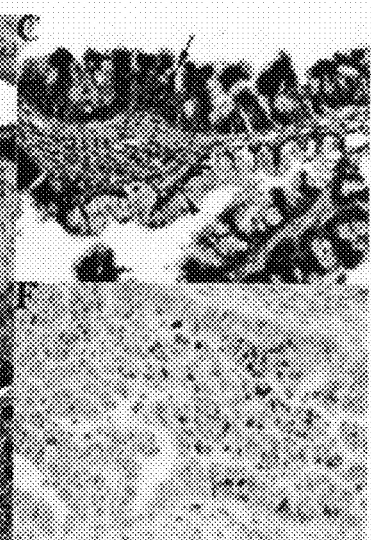
Fig. 9C
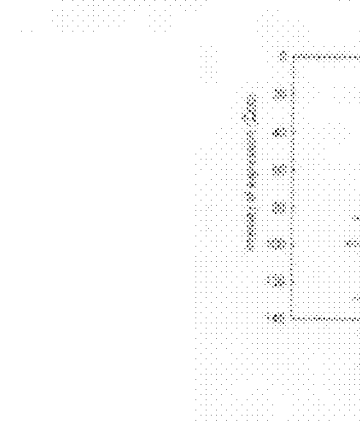
Fig. 9D
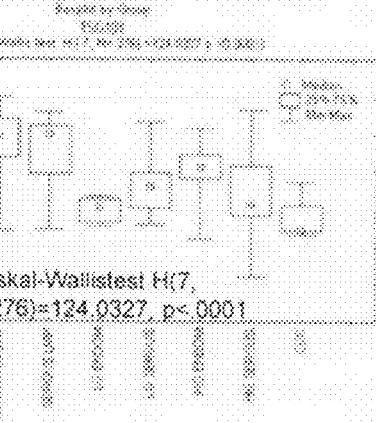
Fig. 9E
Fig. 9F
Fig. 9G

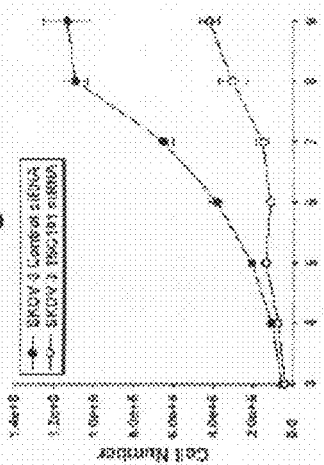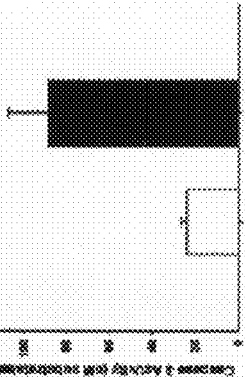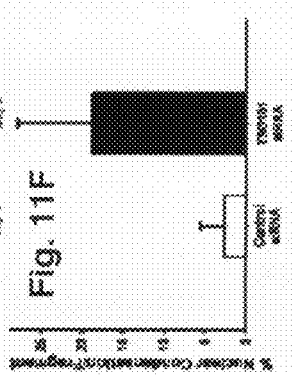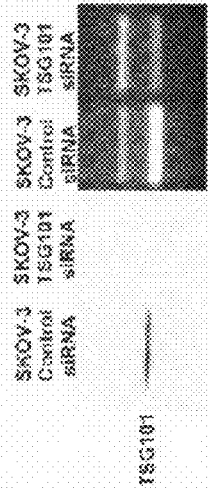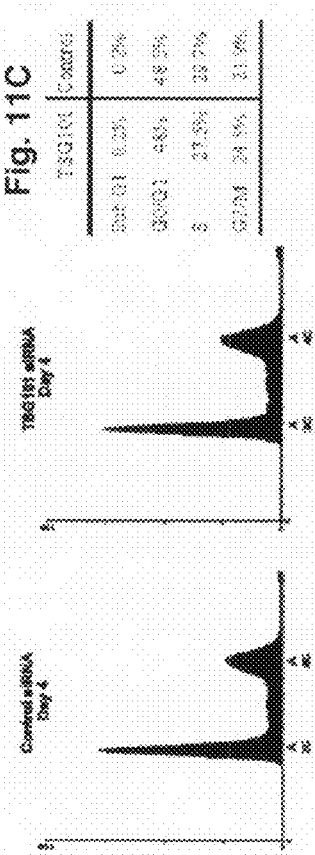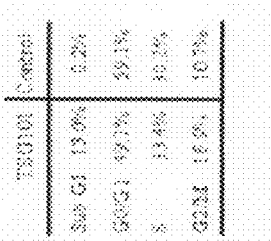

USE OF TUMOR SUSCEPTIBILTY GENE 101 (TSG 101) AS A PROGNOSTIC AND DIAGNOSTIC MARKER

CROSS-REFERENCE TO RELATED APPLICATION

This non-provisional application claims benefit of provisional U.S. Ser. No. 60/772,794, filed Feb. 13, 2006, now abandoned.

FEDERAL FUNDING LEGEND

This invention was supported in part by National Institutes of Health GM066170. Consequently, the federal government has certain rights in this invention.

BACKGROUND OF THE INVENTION

1. Field of the Invention

The present invention relates to the fields of molecular biology, cell signaling and cancer biology. More specifically, the present invention demonstrates the use of TSG101 as biomarker for the diagnosis and prognosis of cancer, especially ovarian cancer.

2. Description of the Related Art

Oncogenic transformation is an intricate process involving alterations of multiple genetic elements and signaling cascades. One critical signaling molecule that contributes directly to transformation is the small G-protein RAS. RAS functions as an intracellular molecular switch, cycling between the GDP-bound inactive state and the GTP-bound active state in response to external stimuli leading from cell surface receptor tyrosine kinases to nuclear transcription factors (Berchuck and Carney, 1997; Marshall, 1995). Several well-known intracellular signaling cascades including the Raf/MEK/ERK pathway, the PI3 kinase pathway, and the Ral-GDS pathway, have been identified as mediators of RAS downstream effects (Feig et al., 1996; Kauffmann-Zeh et al., 1997; Khosravi-far et al., 1996; Shibatohge et al., 1998; Vavvas et al., 1998; Watari et al., 1998). RAS-associated cell signaling is involved in many important cellular processes, such as cell growth, differentiation and survival under physiological conditions. Constitutively active RAS mutants have been found in 30% of all human cancers. RAS or BRAF mutations are involved in 60-70% of low grade serous ovarian cancer (Shih and Kurman., 2004). However, it is still unclear as to how oncogenic RAS mutants, in collaboration with other oncogenes and tumor suppressors, perturb the balance of cellular signaling networks and lead to the formation of cancer cells.

One particular protein implicated in tumorigenic processes that has garnered significant interest in recent years is the tumor susceptibility gene 101 (TSG101), a coiled-coil domain-containing protein that interacts with stathmin in a yeast two-hybrid screen. This gene encodes a multidomain protein that contains a putative DNA-binding motif at its C-terminus and can act as a transcriptional cofactor to repress or activate nuclear hormone receptor-mediated transactivation. The N-terminal region of TSG101 shares an extensive sequence homology to the Ubc domain of ubiquitin-conjugating enzyme (E2) but lacks a critical active-site cysteine residue essential for enzymatic activity, thus suggesting a potential role for TSG101 in regulation of ubiquitin-mediated protein degradation. Several studies have shown TSG101 to be an important cellular factor that specifically recognizes mono-ubiquitinylated proteins and mediates endosomal trafficking that is important for membrane receptor endocytosis and retroviral budding.

The implied tumor suppressor function of TSG101 was proposed based on a homozygous functional knockout study, in which inactivation of TSG101 in NIH3T3 mouse fibroblasts led to focus formation in monolayer cell cultures, anchorage independent growth in soft-agar, and in vivo tumor formation in nude mice (Li and Cohen., 1996). Initial studies suggested that TSG101 was often mutated in human breast cancers (Li et al., 1997) and its aberrant splice variants were frequently detected in different tumor types (Gayther et al., 1997; Lee and Feinberg, 1997; Li et al., 1998; Steiner et al., 1997; Sun et al., 1997; Wang et al., 1998). However, it was determined later that these apparent mutations were in fact alternative splice variants generated exclusively by exon skipping (Wagner et al., 1998). The functional roles of these TSG101 splice variants in normal cellular processes and tumorigenesis remains unsolved.

Although TSG101 is essential for cell proliferation, cell survival and embryonic development under normal physiological conditions (Carstens et al., 2004; Krempler et al., 2002; Ruland et al., 2001; Wagner et al., 2003), the role of TSG101 in tumor formation and development has proven to be complex and remains controversial. For instance, TSG101 was initially discovered as a potential tumor suppressor and the expression of TSG101 has been shown to be decreased in certain cancer samples (Bennett et al., 2001). However, more recent studies suggest that TSG101 levels are elevated in some human cancers, including thyroid (Liu et al., 2002) and gastrointestinal tumors (Koon et al., 2004). Functional proteomic approaches, have recently revealed that TSG101 is overexpressed in a large number of ovarian cancer patients. Although TSG101 was initially recognized as a potential tumor suppressor (Li and Cohen, 1996), the precise role of TSG101 in tumor formation, development, and its relevance to ovarian carcinomas in the clinical settings are largely unknown. Furthermore, overexpression of TSG101 can also lead to neoplastic transformation (Li and Cohen, 1996). Gene silencing of TSG101 leads to growth arrest and cell death in breast and prostate cancer cells (Zhu et al., 2004), instead of growth promotion as would be expected for loss of a true tumor suppressor.

Although it is known that steady-state TSG101 levels are tightly controlled in normal cells, primarily at the post-translational level, keeping protein concentrations within a narrow range (Feng et al., 2000), the mechanism of TSG101 post-translational regulation is not clear. Hence, understanding the cellular regulation of TSG101 is an important task for further elucidating the function of TSG101 under physiological and neoplastic conditions.

Thus, the prior art lacks an understanding of the precise role of TSG101 in human cancer development, its correlation with clinicopathological variables, survival, tumor formation and development specifically in ovarian cancer in clinical settings. The present invention fulfills this long-standing need and desire in the art.

SUMMARY OF THE INVENTION

In one embodiment of the present invention, there is provided a method of diagnosing cancer in the individual. Such a method comprises obtaining a biological sample from the individual and detecting TSG101 in the sample, where the presence of TSG101 either alone or in combination with other markers characteristic of the cancer in the sample is indicative of presence of the cancer in the individual.

In another embodiment of the present invention, there is provided a method of determining the prognosis of a cancer patient. Such a method comprises obtaining a biological sample from the patient and detecting TSG101 in the sample, where the presence of TSG101 either alone or in combination with other markers characteristic of the cancer in the sample indicates that the patient would have a poor prognosis.

In yet another embodiment of the present invention, there is a kit for detecting TSG101 in a sample. Such a kit comprises an antibody, where the antibody is specific for TSG101. In another embodiment of the present invention, there is a method of treating an individual having an overexpression of TSG101 gene or TSG101 gene product, comprising the step of administering to the individual an agent that downregulates the expression of the TSG101 gene or TSG101 gene product.

BRIEF DESCRIPTION OF THE DRAWINGS

FIGS. 1A-E show post-transcriptional regulation of TSG101 by oncogenic RAS. FIG. 1A shows protein levels of TSG101 in T29, T29H and T29K cells revealed by 2-DE gel analysis. FIG. 1B shows quantitative measurement of TSG101 protein levels in T29, T29H and T29K cells (n=4). FIG. 1C shows protein levels of TSG101 in T29H and T29 cells by immunoblotting analysis using TSG101 specific antibodies. FIG. 1D shows mRNA levels of TSG101 in T29 and T29H cells in the presence and absence of the HRAS inhibitor FTI-277 measured by semi-quantitative PCR. FIG. 1E compares TSG101 mRNA expression levels in T29 and T29H cells as determined by real-time PCR analysis from multiple independent purified RNA samples (n=3).

In FIG. 2A, cells were pretreated 24 hrs with FTI-277 (10 μM), U0126 (20 μM), and LY294002 (10 μM). Equal amounts of total cellular proteins were run on 12% SDS-PAGE, transferred to PVDF membranes and probed with TSG101 antibody. In FIG. 2B, cells were stably transfected with retroviral shRNA constructs against either $HRAS^{V12}$ only (H1) or both wildtype and oncogenic RAS (H2) and cell lysates on PVDF membranes were probed with TSG101 antibody. Equal protein loading was determined by Ponceau S staining of PVDF membranes. In FIG. 2C, SKOV-3 cells were transfected with H2 shRNA. Cell lysates were harvested, separated by 12% SDS-PAGE, transferred to PVDF membranes, and probed with TSG101 antibody. Gel images are representative of three independent experiments.

FIGS. 3A-C show dependence of RAS-mediated TSG101 modulation on $p14^{ARF}$/HDM2. In FIG. 3A, total cellular levels of $p14^{ARF}$ in T29 and T29H cells was measured by immunoblotting using $p14^{ARF}$ specific antibody. In FIG. 3B, total and cytoplasmic levels of TSG101 from T29 cells were compared with those of T29H cells and T29H cells stably transfected with H1 and H2 retroviral shRNA. In FIG. 3C, total protein levels of HDM2 and TSG101 from T29H cells and T29H cells stably expressing ectopic HDM2. Similar results were obtained from two independent experiments.

In FIG. 5A, siRNA transfected SKOV-3 cells were plated at $2\times10^3$ cells/well in 96 well plates and viability was monitored three days post-transfection over a five-day period using MTT assay. Each data point represents an average of five independent readings ±SD. FIG. 5B shows that TSG101 siRNA Knockdown reduced tumor growth of SKOV-3 cells in nude mice. Control (black bars) or TSG101 siRNA (open bars) transfected SKOV-3 cells were injected into the right and left flanks (respectively) of 4-6 week old Balb/c athymic nude mice on da) three following siRNA transfection. Tumor volume was monitored over 4 weeks, after which time tumors were excised and measured to determine final overall growth.

FIG. 6A shows levels of CITED2 and HIF-1α mRNA monitored by RT-PCR in SKOV-3 cells beginning 3 days post-transfection with either control or TSG101 siRNA. FIG. 6B shows cellular levels of CITED2 protein monitored by immunoblotting analysis using antibody specific against CITED2.

In FIG. 7A, transcriptional activation was measured by expression of HRE-GFP reporter construct in SKOV-3 cells. The SKOV-3 mounted on coverslips that were earlier transfected with TSG101 or control siRNA were further transfected with HRE-GFP (3 days post siRNA transfection). Two days following HRE-GFP transfection (5 days post siRNA transfection), GFP fluorescence was determined using a fluorescence microscope equipped with a digital camera. In FIG. 7B, SKOV-3 cells transfected with control or TSG101 siRNA, and subsequently with HRE-GFP, were lysed on day 5. HIF-1α transcriptional activation was measured as a function of GFP protein levels probed using a GFP antibody (1:1000).

FIGS. 9A-G show levels of TSG101 in Human Ovarian Carcinomas. FIG. 9A shows negative expression in normal ovarian surface epithelial (40×). FIG. 9B shows negative and positive expressions of TSG101 in normal ovarian surface epithelial (arrow head) and in adjacent serous carcinoma (arrow, 15×), respectively. FIG. 9C shows weak to negative expression in a mucinous cystadenoma (arrow head) with strong positive expression in adjacent mucinous LMP (15×). FIG. 9D shows positive expression in a high grade endometrioid carcinoma (40×). FIG. 9E shows strong positive expression in a high grade serous carcinoma (40×). FIG. 9F shows positive nuclear staining for p21 in a serous carcinoma. FIG. 9G shows TSG101 box plot by groups. The relative optical density of the expression of the marker was measured and analyzed using a non parametric analysis in normal ovarian surface epithelial and ovarian tumors. LG: low grade; HG: high grade; LMP: low malignant potential; CCC: clear cell carcinoma.

FIGS. 11A-F show association of suppression of TSG101 expression with cell cycle arrest and growth inhibition. In FIG. 11A, SKOV-3 cells were transfected with TSG101 and control siRNAs and RNA and protein were isolated 48 hours post transfection. Levels of mRNA were determined by semi-quantitative RT-PCR and protein levels were determined by immunoblotting, respectively. Similar results were obtained from more than 4 independent experiments. In FIG. 11B, TSG101 or control siRNA transfected cells were plated at 2.5×10$^4$ cells/well in 6 well plates and cell growth was determined by counting over successive days. Each data point represents the average of 3 wells. Control and TSG101 knockdown SKOV-3 cells were stained with propidium iodide and analyzed by FACS on day 4 (FIG. 11C) or day 6 (FIG. 11D) following transfection. Sub G1 cells are calculated as a supplemental population. In FIG. 11E, SKOV-3 cell lysates were obtained 6 days following transfection with control or TSG101 siRNA. Caspase activity was determined using the fluorogenic substrate DEVD-AFC. In FIG. 11F, control and TSG101 knockdown SKOV-3 cells on day 5 following siRNA transfection were stained using Hoechst 22658 and Nuclear condensation was observed on a fluorescent microscope. Cells with condensed/fragmented DNA were quantified from at least 8 images, and represented as a percentage of the total number of cells.

FIG. 12A shows levels of p21 mRNA monitored by RT-PCR in SKOV-3 cells beginning 3 days post-transfection with either control (Con) or TSG101 siRNA (TSG). FIG. 12B shows p21 protein levels measured by immunoblotting analysis using a p21-specific antibody. FIG. 12C shows suppression of TSG101 by siRNA potentiates p21 transcription in a p53-independent manner. FIG. 12D shows p21 promoter element as detected by PCR in SKOV-3 cells that were transfected with control or TSG101 siRNA, protein-DNA complexes were immunoprecipitated with TSG101 antibody.

DETAILED DESCRIPTION OF THE INVENTION

The goal of the present invention was to demonstrate the feasibility of using TSG101 as a biomarker for the diagnosis and prognosis of cancer, specifically ovarian cancer. In this regard, the present invention demonstrated that the expression of TSG101 was increasingly positive in borderline tumors, low grade and high grade ovarian carcinomas while normal ovarian epithelial cells did not show significant expression of TSG101. Additionally, increased expression of TSG101 was also associated with poor survival of patients.

Collaboration among oncogenes and tumor suppressors represents a key mechanism of oncogenic transformation. A recent study suggested that oncogene RAS plays an important role in the epigenetic inactivation of opioid binding protein/cell adhesion molecule-like gene (OPCML), a recently identified tumor-suppressor in human epithelial ovarian cancer (Mei et al., 2005). The present invention used a 2DE-based functional proteomic approach to identify TSG101 as a protein that was significantly altered post-transcriptionally following transformation of human ovarian surface epithelial cells with oncogenic RAS. This is the first report linking RAS signaling and TSG101 regulation.

Figure 8:
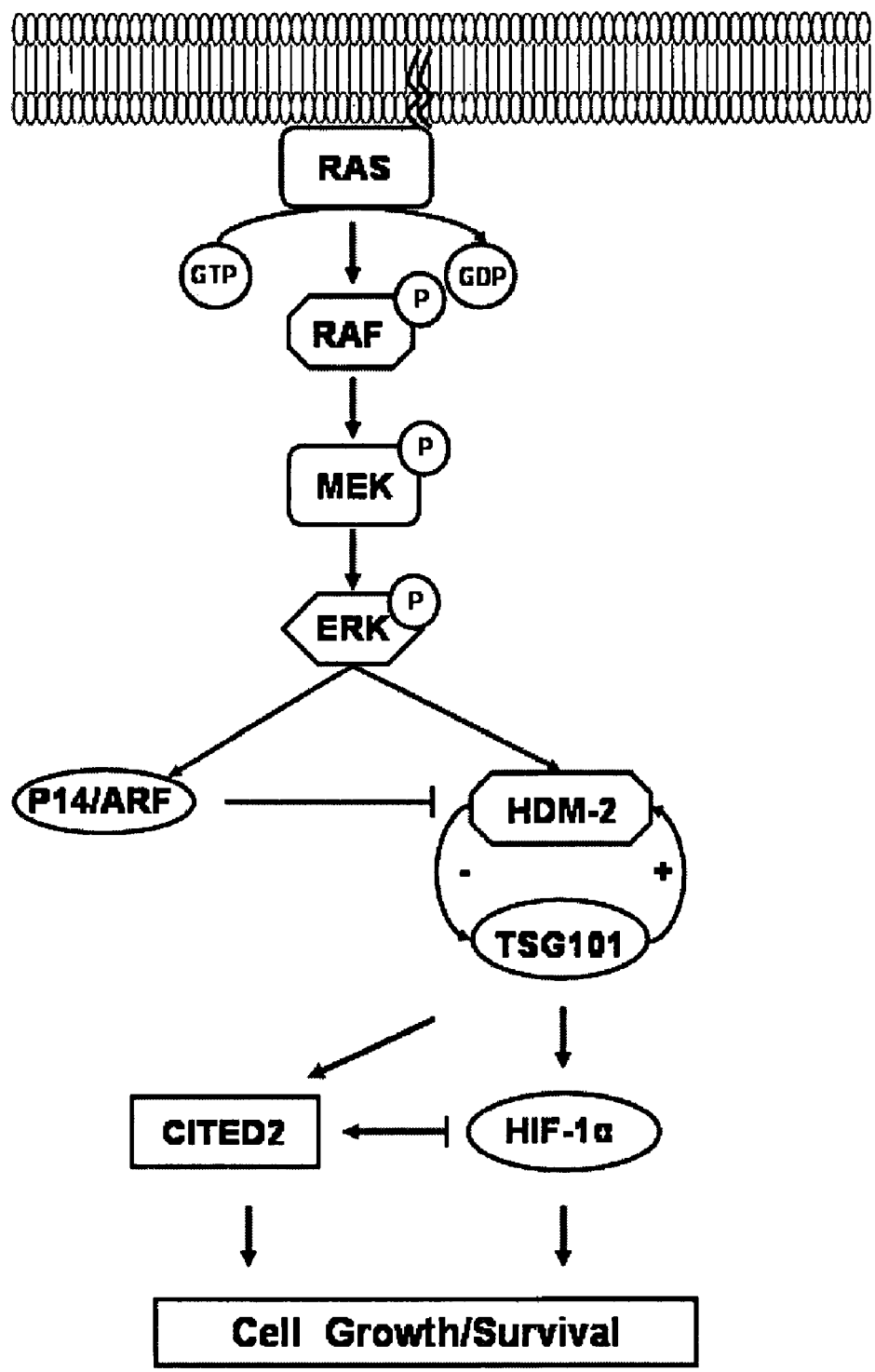
FIG. 8 shows mechanism of RAS-mediated TSG101 regulation. Activation of the RAS/RAF/MEK/MAP kinase leads to transcriptional induction of $p14^{ARF}$ that suppresses cellular HDM2 activity. Inactivation of HDM2 leads to elevated cellular levels of TSG101 through a negative-feedback loop. Increased TSG101 levels in ovarian cancer cells enhance CITED2/HIF-1α expression and activation, and subsequently promote cell growth and survival.

A primary mechanism for TSG101 protein regulation occurred at the level of protein degradation (Feng et al., 2000), and TSG101 and MDM2 formed a negative autoregulatory loop that modulated the cellular levels of both proteins (Li et al., 2001). The present invention demonstrated that oncogenic RAS through the RAF/MEK/ERK signaling cascade as shown (Palmero et al., 1998), upregulated p14$^{ARF}$, which in turn suppressed cellular activity of MDM2 and consequently led to the increase of cellular TSG101 protein levels in RAS-transformed cells (FIG. 8). The clinical significance of the RAS-mediated TSG101 upregulation was clearly demonstrated by the finding that the expression of TSG101 was increasingly positive in low-grade tumors and high grade carcinomas while normal ovarian epithelial cells show negative staining for TSG101. The ability to detect protein expression alterations in human ovarian carcinomas using a genetically-defined cancer model and functional proteomics further validated the physiological relevance of this model and the value of the proteomic approach in cancer study.

To determine the significance of TSG101 upregulation and the role that TSG101 may play in tumor formation and development in human ovarian cancer, a siRNA was used to knock down TSG101 in the ovarian carcinoma cell line SKOV-3 with hyperactivated RAS signaling pathways similar to the engineered T29H cells (Yang et al., 2003). SKOV-3 cells exhibited significant growth inhibition and underwent apoptosis approximately 5 days following transfection with TSG101 siRNA. In addition, when injected into athymic nude mice, SKOV-3 cells with TSG101 silenced induced significantly smaller tumors in vivo, suggesting that TSG101 had a definitive prosurvival effect on this ovarian epithelial cancer cell line. These findings are in agreement with recent data pointing to a more growth promoting rather than tumor suppressive effect of TSG101 as proposed earlier (Carstens et al., 2004; Krempler et al., 2002; Zhu et al., 2004).

Suppression of TSG101 expression in SKOV-3 cells was accompanied by the reduction of CITED2 and HIF-1α, two closely related transcriptional regulators that play important roles in the regulation of cell growth and survival. Gene knockout of Cited2 in mice resulted in embryonic lethality and premature senescence of the Cited2$^{-/-}$ mouse embryonic fibroblasts with increased expression of the cell proliferation inhibitors p16$^{INK4a}$, p19$^{ARF}$, and p15$^{INK4b}$ (Krane et al., 2003; Yin et al., 2002), while overexpression of CITED2 in Rat1 cells led to anchorage-independent growth in soft agar and tumor formation in nude mice (Sun et al., 1998). These observations suggested that CITED2 was essential for cell proliferation and survival. On the other hand, hypoxia inducible factor HIF-1α controls the expression of more than 70 genes (Mazure et al., 2004), plays a critical role in cancer cell survival (Semenza, 2003) and tumor migration and metastasis (Pennacchietti et al., 2003; Yang et al., 2004). In addition to their individual roles in transcription regulation, HIF-1α and CITED2 have also been shown to operate in a negative feedback loop through a common interaction with CBP/p300: HIF-1α transcribes CITED2 during hypoxia, and accumulation of CITED2 inhibits HIF-1α transactivation by blocking its interaction with CBP/p300 and restores normal oxygen homeostasis (Tien et al., 2004). Given the important roles that CITED2 and HIF-1α play in cell proliferation and survival, the apparent growth inhibitory and apoptotic effects of TSG101 gene silencing observed in the SKOV-3 cells may be partially mediated by the loss of CITED2/HIF-1α expression.

The present invention identified a novel mechanism of TSG101 regulation through the RAS signaling pathway. This regulatory mechanism appeared to be post-translational in nature and likely involved p14$^{ARF}$/HDM2. Thus, the RAS mediated up regulation of TSG101 provided pro-growth/survival stimuli through the modulation of transcription regulators such as HIF-1α and CITED2 (FIG. 8). This observation was consistent with the findings that induction HIF-1α by oncogenic RAS via the RAF/MEK/MAPK pathway was important for RAS-mediated tumor promotion (Lim et al., 2004) and inhibition of RAS activation in glioblastoma led to down-regulation of HIF-1α and cell death (Blum et al., 2005). Based on the results disclosed herein, it is contemplated that the connection among oncogenic RAS, TSG101, and HIF-1α/CITED2 might play an important role for RAS-mediated oncogenic transformation through regulation of CBP/p300-interacting transactivator with ED-rich tail 2 (CITED 2) and hypoxia-inducible factor 1α since it has been shown that loss of HIF-1α negatively affected tumor growth in oncogenic RAS transformed cell lines (Ryan et al., 2000). The present invention also demonstrates that TSG101 was overexpressed in ovarian carcinomas and might represent a potential target for future therapeutic intervention to inhibit growth and precipitate apoptosis of cancer cells.

The present invention also demonstrated that TSG101 negatively regulated p21 contributing to ovarian carcinoma development and prognosis. These results for the first time demonstrate that TSG101, in contrary to the notion of a potential tumor suppressor gene, was a promoting factor for ovarian tumor progression. TSG101 is an essential protein that is involved in numerous cellular processes such as transcriptional regulation, protein degradation/ubiquitination, cell cycle control, vesicular sorting/transport, and viral budding. The cellular levels of TSG101 are tightly kept within a narrow range under physiologic conditions and complete knockout of TSG101 leads to embryonic lethality in mice and cell cycle arrest and cell death in cultured cell lines (Ruland et al., 2001; Wagner et al., 2003; Krempler et al., 2001).

Although it was originally identified as a potential tumor suppressor gene whose homozygous deletion led to transformation in NIH3T3 cells (Li and Cohen, 1996), the precise roles of TSG101 in tumorigenesis remained to be defined. TSG101 was also identified as a down-stream target of oncogenic RAS upregulated during in vitro transformation of human ovarian epithelial cells (Young et al., 2005; Young et al., 2004). Interestingly, this apparent increased expression of TSG101, observed in an vitro model system, was also preserved in ovarian cancer patients since more than 70% of ovarian carcinomas expressed elevated levels of TSG101. These observations are in agreement with several recent studies that show that TSG101 levels are elevated in certain human cancers, including thyroid (Liu et al., 2002) and gastrointestinal tumors (Koon et al., 2004), and gene silencing of TSG101 leads to growth arrest and cell death in breast and prostate cancer cells (Zhu et al., 2004).

Additionally, the present invention also demonstrated that increased TSG101 concentration was associated with poor prognostic outcomes. The tumor promoting effects of TSG101 in EOC was mediated at least in part through the suppression of a tumor suppressor, cyclin-dependent kinase inhibitor p21, since the results disclosed herein clearly showed the recruitment of TSG101 to the p21 promoter where TSG101 acts as corepressor of p21 transcription in ovarian cancer cells. This was further supported by the finding that the levels of TSG101 and p21 were inversely correlated in human ovarian tumor samples.

Further, the observations that patients with lower TSG101 score had significantly higher rates of high p21 score and high TSG101 levels were associated with poor prognosis are consistent with an early study reporting high p21 expression to be a favorable disease outcome in EOC (Anttila et al., 1999). It is known that p21, a mediator of p53 tumor suppression inhibits cyclin-dependent kinases and leads to G1/S cell cycle arrest (el Deiry et al., 1993; Harper et al., 1993). While in wild-type p53-containing tumor cells, p21 is induced in p53-mediated G1 arrest and apoptosis (el Deiry et al., 1994), p53-independent induction of p21 in various cancer cells (Sheikh et al., 1994; Zhang et al., 1995), including ovarian cancer cells (Elbendary et al., 1994) and in p53-knockout mice (Michieli et al., 1994) has also been demonstrated. Connections between TSG101 and p21 have been made previously as homozygous deletion of tsg101 in mice led to a dramatic increase of p53 with concomitant accumulation of its down-stream effector p21 and embryonic lethality (Ruland et al., 2001; Wagner et al., 2003). Increase of p21 expression by silencing TSG101 in these studies was believed to be mediated by p53 through an autoregulatory feedback loop between TSG101 and MDM2/p53, in which TSG101 suppresses MDM2 ubiquitination and degradation, and consequent down-regulation of p53 protein (Li et al., 2001). However, a more recent study suggests that while p21 was a mediator of the cell arrest in tsg101 knockout cells, deletion of tsg101 had no effect on MDM2 steady-state levels and null mutation of p53 did not rescue the tsg101 deficiency phenotype (Carstens et al., 2004), thereby suggesting that the proposed feedback loop between TSG101 and MDM2/p53 was not the mechanism for TSG101-mediated p21 regulation. Alternatively, TSG101 has been implicated to negatively regulate cell proliferation through direct association and stabilization of p21 (Oh et al., 2002). Nevertheless, this notion is not consistent with majority of the studies showing TSG101 is essential for cell proliferation. In this regard, the results discussed herein show that TSG101 acting as a transcriptional suppressor of p21 provides an important link for understanding the role of TSG101 in cell growth and proliferation.

In summary, the present invention demonstrated that TSG101 negatively regulates the tumor suppressor protein p21 and played an important role in tumor progression of ovarian carcinomas since increased TSG101 protein levels were observed to be associated with late stage and high grade EOC. Additionally, TSG101 seemed to contribute to tumor aggressiveness as high TSG101 protein levels were correlated with reduced patient survival. Taken together, the results discussed herein suggested that elevated TSG101 was associated with poor prognosis and a potential therapeutic target for EOC.

Overall, the present invention demonstrates that TSG101 plays an important role in development of cancer, specifically ovarian cancer and patient survival and that the expression level of TSG101 could be used as a prognostic and diagnostic marker for ovarian cancer for the following reasons: First, the present invention demonstrated elevated expression level of TSG101 in human ovarian epithelial cells transformed by oncogenic RAS via a proteomic study of a genetically defined human ovarian cancer model. The clinical association of RAS-mediated TSG101 upregulation in human ovarian surface epithelial cells was examined using human ovarian cancer tissue arrays that contained 422 samples. While normal ovarian epithelial cells did not show significant expression for TSG101, the expression of TSG101 was increasingly positive in borderline tumors, low grade and high grade carcinomas.

Second, the present invention also demonstrated that patients with low expression of TSG101 survive longer that those with high expression of TSG101. Silencing of TSG101 gene expression by TSG101-specific siRNA in SKOV-3 cell, decreased cell proliferation, increased G2/M arrest and apoptosis, and suppressed tumor growth in nude mice. Third, the present invention also demonstrated that suppression of TSG101 in SKOV-3 cells was accompanied by a dramatic increased expression of tumor suppressor p21 both at mRNA and protein levels. Fourth, the regulatory relationship between TSG101 and p21 observed in vitro models was conserved in patient samples since Chi-square Test revealed that TSG101 levels were significantly associated with P21 levels in ovarian cancer patients (p value 0.02). Patients with lower TSG101 expression levels had a significantly higher rate of high p21 levels and markers TSG101 and p21 are significantly correlated with spearman rank correlation −0.11 and p value 0.04. Fifth, TSG101 was also shown to be secreted in culture medium and patient serum.

The present invention is directed to a method of diagnosing cancer in an individual. This method comprises obtaining a biological sample from the individual, and detecting TSG101 in the sample, wherein the presence of TSG101 either alone or in combination with other markers characteristic of the cancer in the sample is indicative of presence of the cancer in the individual. Generally, the biological sample is a tumor tissue biopsy, fine needle aspiration biopsy, whole blood, serum, or plasma. Furthermore, examples of the methods used to detect TSG101 in the sample includes and is not limited to Northern Blot, Western Blot, PCR, dot blot, ELISA sandwich assay, radioimmunoassay, DNA array chips, flow cytometry, SELDI-TOF, mass spectrometry, protein array and other proteomic assays. The cancer that the individual has exhibits overexpression/mutation of TSG101, overexpression/mutation of Ras underexpression/mutation of p21 or a combination thereof. It may also exhibit expression of any other gene that is upstream or downstream of the TSG101 gene in the cell signaling pathway. Examples of cancer that show such characteristics include but are not limited to ovarian cancer, gastric cancer, thyroid cancer, prostate cancer, cervical cancer, liver cancer, lung cancer or pancreatic cancer. The markers characteristic of the cancer are Ras, CA 125 (ovarian cancer), CA 15-3 and 27-29 (breast cancer), CEA; Carcinogenic Embryonic Antigen (colon, lung, breast, pancreas, and gastrointestinal tract cancers), PSA (prostate cancer), AFP; α-fetoprotein (liver cancer), CA 19-9 and CEACAM 1 (pancreatic cancer).

The present invention is also directed to a method of determining the prognosis of a cancer patient, comprising: obtaining a biological sample from the patient and detecting TSG101 in the sample, where the presence of TSG101 either alone or in combination with other markers characteristic of the cancer indicates that the patient would have poor prognosis. All other aspects regarding the type of sample, method of detecting TSG101, type of cancer and markers are as discussed supra. The present invention is further directed to a kit for detecting TSG101 in a sample, comprising an antibody, specific for TSG101 or a labeling agent specific for TSG101. The labeling agent may be a protein, a DNA or a RNA. Examples of such a labeling agent includes but are not limited to aptamer, thioaptamer (a modified aptamer) that is specific for TSG101. The kit further comprises means to detect the antibody or the labeling agent.

The present invention is still further directed to a method of treating an individual having overexpression of tsg101 gene or TSG101 gene product, comprising the step of administering to the individual an agent that downregulates the expression of the tsg101 gene or TSG101 gene product, or inhibits the activity of TSG101 gene products. The examples of the agents that downregulate the expression of tsg101 gene include but is not limited to a peptide nucleic acid, siRNA, an aptamer, a modified aptamer or an anti-sense RNA/DNA and the agents that downregulates the expression of TSG101 gene product or inhibits the activity of the TSG101 gene product includes but is not limited to an antibody or a small molecule inhibitor. Examples of the cancer that the individual has including the genes that are overexpressed, underexpressed or mutated are as discussed supra.

The following examples are given for the purpose of illustrating various embodiments of the invention and are not meant to limit the present invention in any fashion. One skilled in the art will, appreciate readily that the present invention is well adapted to carry out the objects and obtain the ends and advantages mentioned, as well as those objects, ends and advantages inherent herein. Changes therein and other uses which are encompassed within the spirit of the invention as defined by the scope of the claims will occur to those skilled in the art.

EXAMPLE 1

Cell Cultures

Transformed T29H and T29K cells were generated through retroviral transfection of immortalized human ovarian surface epithelial cells T29 with oncogene $HRAS^{V12}$ and $KRAS^{V12}$, respectively, as described previously (Liu et al., 2004). These cells were grown in Media 199/MCDB105 media (1:1) (Sigma-Aldrich) containing 10% FBS and 1% Penicillin/Streptomycin (Gibco BRL). SKOV-3 cells were maintained in RPMI 1640 media containing 5% FBS (Gibco BRL) and 1% Penicillin/Streptomycin (Gibco BRL).

EXAMPLE 2

Two Dimensional Electrophoresis (2-DE) Analysis

2-DE proteomic analysis was performed as described (Young et al., 2005; Young et al., 2004). Briefly, cells were trypsinized, washed in PBS, and lysed in buffer containing the following: 7 M Urea, 2 M Thiourea, 4% CHAPS, 1 mM EDTA, 1 mM EGTA, 60 mM DTT 1 mM PMSF, 25 μg/ml leupeptin, 10 μg/ml aprotinin, 1 mM benzamidine, 1 mM sodium orthovanadate, and 1 mM microscystin. Total protein concentration was determined using Bradford assay (Bio-Rad). 200 or 500 μg protein was loaded onto 18 cm immobilin pH gradient strips (GE Biosciences) for analytical or preparative gels, respectively. After focusing for 56,000 Vh, strips were loaded onto 10% SDS-Tricine gels, and electrophoresed for 20 h at 140 V. Gels for image analysis and for spot excision were stained with silver as described, respectively (Blum et al., 1987; Shevchenko et al., 1996). Images were analyzed using Phoretix 2-DE software (Nonlinear Dynamics). Spots of interest were excised and in-gel digested with trypsin as described previously (Young et al., 2004). Proteins were identified by MALDI-TOF analysis by comparison of tryptic fragment profiles with the NCBI database for theoretical peptide cleavage patterns.

EXAMPLE 3

Immunoblotting Analysis

Protein concentrations of cell lysates were assayed with the Bio-Rad protein assay reagent. Equal amounts of protein were loaded onto 12% SDS polyacrylamide mini-gels (Bio-Rad) or 10% Tricine-SDS gels and transferred to PVDF membranes. PVDF blots and the remaining polyacrylamide gels were stained with Ponceau S and Coomassie Blue, respectively, to ensure equal loading and even transfer of the samples. After being blocked overnight in 5% milk in TBS-Tween, blots were incubated with corresponding primary antibodies for 1.5 hrs, followed by HRP-conjugated secondary antibody (1:4000, Bio-Rad) for 45 min. Antigen-antibody complexes were detected by enhanced chemiluminescence (Pierce).

EXAMPLE 4

Gene Expression Analysis

Total RNA was isolated from cells using Trizol reagent (Invitrogen), and concentration was determined by absorbance at 260 nm. Real-Time PCR analysis was carried out using fluorescent TSG101 primers on an Applied Biosystems Prism 7000 Sequence Detection System. RT-PCR was carried out for TSG101 and HIF-1α using 1 μg of isolated total RNA under the following parameters: 94° C. 1 min, 57° C. 1 min and 72° C. 1.5 min, 35 cycles. Primers used for RT-PCR were TSG10 forward 5'-TCCAGTCTTCTCTCGTCCTATTTC-3' (SEQ ID NO: 1), reverse 5'-TTTCCTCC TTCATCCGC-CATCTC-3' (SEQ ID NO: 2), CITED2 forward 5'-GGCG-GCTCTGGCAGCAGCTC-3' (SEQ ID NO: 3), reverse 5'-CGGGCAGCTCCTTGATGCGG-3' (SEQ ID NO: 4), HIF-1a aforward 5'-CCTGCACTCAATCAAGAATTGC-3' (SEQ ID NO: 5), reverse 5'-TTCCTGCTCTGTTTGGT-GAGGCT-3' (SEQ ID NO: 6).

EXAMPLE 5

Ras Pathway Inhibitors Studies

For chemical inhibitor experiments, cells were grown to 50-60% confluence in 6 well plates and treated with the following or DMSO vehicle, 20 μM U0126 (MEK inhibitor), 10 μM LY294002 (PI3K inhibitor), or 10 μM FTI-277 (farnesylation inhibitor) for 24 hours. Following treatments, cells were lysed and the levels of total and cytoplasmic TSG101 were examined by immunoblotting using specific anti-TSG101 antibody (1:1000, Novus).

EXAMPLE 6

Inhibition of HRAS Gene Expression by Retroviral siRNA

SKOV-3 and T29H cells were transfected with two retrovirus-mediated HRAS siRNA vectors (designated H1 and H2) that have been described previously (Yang et al., 2003). Briefly, H1 selectively silences mutant HRAS$^{V12}$ while H2 suppresses both the HRAS$^{V12}$ mutant and wild-type HRAS expression. SKOV-3 and T29H cells grown to 50% confluence in 10 cm plates were infected with H1 and H2 retroviral supernatants generated from Phoenix viral packaging cells. Following infection, cells were selected for 10 days in 0.7 mg/ml of G418 to establish stable cell lines. Raf-GTP binding assays and western blotting using anti-HRAS (1:2000, Santa Cruz) were used to measure the expression and activation levels of RAS proteins in these siRNA cell lines.

EXAMPLE 7

Overexpression of HDM2 in T29H and SKOV-3 Cells

Freshly plated T29H cells ($2\times10^5$ cells/plate in 6 cm plates) and SKOV-3 cells at 80% confluence were transfected with HDM2 vector (1 μg) using Lipofectamine 2000 (Invitrogen) as per manufacturer's instructions. Cells were harvested at 24 and 48 hrs post transfection, or further selected for the generation of stable lines using 0.7 mg/ml G418. Whole cell lysates were processed as described above and western blots were probed using anti-HDM2 (1:1000, Santa Cruz).

EXAMPLE 8

TSG101 RNA Interference

A siRNA duplex specific for TSG101 (targeting TSG101 coding sequence 413-433) and a scrambled random control siRNA with matching GC content were obtained from Dharmacon. This specific TSG101 siRNA duplex (sense: CCUC-CAGUCUUCUCUCGUCdTdT (SEQ ID NO: 7) and antisense: dTdTGGAGGUCAGAAGAGAGCAG (SEQ ID NO: 8) have been successfully applied to suppress the expression of endogenous TSG101 in several high quality studies (Amit et al., 2004; Garrus et al., 2001; Hewitt et al., 2002; Ismaili et al., 2005). Transfection of the siRNAs was according to the manufacturer's instructions using Lipofectamine 2000 (Invitrogen).

EXAMPLE 9

HIF-1α GFP Reporter Assay

Cells were plated at $1\times10^5$ in 3.5 cm wells and grown overnight at 37° C. The following day cells were transfected with 375 ng/well of either TSG101 or control siRNA duplex using Lipofectamine 2000. Cells were then passaged at 48 hrs post-transfection and used for subsequent experiments. The HIF-1α response element (HRE)-GFP reporter (a generous gift from Mark Dewhirst) was transfected into cells 48 hrs after transfection with siRNA reagents, and subsequently plated onto microscope cover slips. On the fifth day following siRNA transfection, cells on cover slips were rinsed in PBS and fixed in 2% paraformaldehyde for 15 min. Nuclear staining was carried out with DAPI (5 ng/ml) for 5 min, after which slides were mounted and observed using a fluorescence microscope (Olympus BX51) equipped with a Hamamatsu digital camera (C4742-95).

EXAMPLE 10

Cell Growth and Viability Assays

SKOV-3 cells were trypsinized 48 hrs post-transfection with siRNAs and plated at $2\times10^3$ cells/well in 96 well plates, with 5 wells for each treatment. On subsequent days (days 3 to 7), media was removed and 100 μl/well fresh media was added along with 10 μl of 3-(4,5-dimethylthiazol-2-yl)-2,5-diphenyl tetrazolium bromide (MTT) to a final concentration of 500 μg/ml. Cells were incubated for 3 hrs at 37° C., and then lysed by adding 200 μl/well DMSO and incubating at 37° C. for 1 hr. Cell viability was measured by reduction of MTT, which registered absorbance at 595 nm on a Molecular Devices microplate reader.

EXAMPLE 11

In Vivo Tumor Assays

SKOV-3 cells were trypsinized 3 days following transfection with either Control or TSG101 siRNA, and subsequently washed and resuspended in phosphate-buffered saline at $5\times10^6$ cells/ml. 200 μl ($1\times10^6$ cells) of control or TSG101 transfected SKOV-3 cells were injected s.c. into the right and left flanks (respectively) of 4-6 week old Balb/c athymic nude mice (Jackson Laboratory, Bar Harbor, Me.). Mice were examined every 5 days until visible tumors appeared. Subsequently, tumor volume measurements were taken every 3-5 days, and mice were sacrificed 6 weeks after initial injections, and a final measurement of tumor volume was taken.

EXAMPLE 12

Upregulation of TSG101 in RAS$^{V12}$ Transformed Human Ovarian Epithelial Cells Revealed by 2-DE Based Proteomic Analysis Equal amount (200 μg) of total cell lysates from pooled early passages of T29 and T29H cells were analyzed by 2-DE based proteomics. At least four gels from two independent cell lysates were used for each cell line. The intensity of protein spots on each gel was determined, normalized to the sum of intensities of all spots on the gel, and quantified as a percentage volume in each gel using Phoretix 2-D analysis software (Nonlinear). Each individual protein spot was then matched with the identical protein spot from replicate gels.

Data for these matched spots were then averaged over all gels for each cell line. The average normalized volume of each spot in the transformed T29H cells was then compared to that of the matched spot in immortalized T29 cells, respectively.

Such an analysis as discussed in an earlier study, TSG101 was identified as a protein up-regulated in the HRAS$^{V12}$ transformed ovarian epithelial cell line (Young et al., 2005). In the present invention, the protein level of TSG101 was up-regulated approximately 2 fold in T29H cells as compared to its immortalized counterpart T29 cells (FIGS. 1A & 1B). This up-regulation was further confirmed by immunoblotting analysis of equal amount of independent total protein lysates from pooled T29 and T29H cells using an antibody specific to TSG101 (FIG. 1C). To check if the apparent increase in TSG101 protein was due to the transcriptional regulation of the TSG101 gene, the levels of TSG101 mRNA in T29 and T29H cells were examined by semiquantitive (FIG. 1D) and real-time PCRs (FIG. 1E). Both methods showed no significant change in TSG101 mRNA levels between T29 and T29H cells. Furthermore, the levels of TSG101 mRNA were not affected by FTI-277, a farnesyl transferase inhibitor that blocks the activation of RAS (FIG. 1D). Taken together, these observations indicated that the regulation of TSG101 occurred at the post-transcriptional level in HRAS$^{V12}$ transformed human ovarian epithelial cells. This observation was consistent with an earlier mRNA expression array study showing the transcription levels of TSG101 were not significantly different in T29 and T29H cells (Liu et al., 2004).

To further determine if the change in TSG101 levels was a direct effect of elevated RAS activity in T29H cells, the TSG101 protein levels were examined in response to FTI-277, a pharmacological inhibitor that represses HRAS activation by inhibiting the farnesylation of HRAS (Hancock et al., 1990). While FTI-277 significantly inhibited RAS-GTP levels in T29H cells as measured by RAS activation assay using GST-tagged Raf-RBD protein (data not shown), FTI-277 caused a significant decrease of TSG101 in T29H cells (FIG. 2A), suggesting that TSG 101 up-regulation was directly linked to the level of HRAS activation. Due to the fact that FTI-277 is a general farnesyl-transferase inhibitor and could cause cellular effects other than HRAS inhibition, a retrovirus based siRNA technique was used to specifically inhibit HRAS activity. H1 shRNA inhibits oncogenic HRAS$^{V12}$ specifically, and the H2 shRNA vector suppresses both endogenous wild-type and oncogenic HRAS (Young et al., 2004). Significant reduction in the levels of TSG101 protein was observed in T29H cells stably transfected with H1 and H2 (FIG. 2B), confirming that HRAS was indeed directly responsible for the up-regulation of TSG101 in this cell line.

EXAMPLE 13

Regulation of TSG101 by RAF/MEK/MAPK Pathway

Figure 2A:
FIGS. 2A-C show that TSG101 up-regulation was HRAS specific and mediated through the MEK/ERK signaling pathway.
Figure 2B:

To dissect the cellular signaling mechanism by which HRAS impinges on TSG101 regulation, inhibitors for known RAS effector pathways were used. MEK inhibitor U0126 significantly decreased cellular TSG101 to levels similar to that of untransformed T29 cells and cells treated with FTI-277, while the PI3 kinase inhibitor LY294002 showed minimal effects on TSG101 levels (FIG. 2A). These results indicated that oncogenic HRAS$^{V12}$ signaling through MEK and not PI3K kinase up-regulated TSG101 post-transcriptionally.

Figure 2C:

To ensure that HRAS-mediated post-transcriptional regulation of TSG101 did not just occur in the genetically defined T29H human ovarian cancer cell model, the effect of altering HRAS activity on modulation of TSG101 was examined in a natural ovarian cancer cell line, SKOV-3. This cell line does not contain an oncogenic RAS allele, but nonetheless exhibits elevated levels of RAS activity (Yang et al., 2003). While expressed at similar levels as T29H cells, TSG101 protein levels in SKOV-3 cells showed a marked decrease following specific gene silencing of endogenous RAS with H2 shRNA (FIG. 2C). These data suggested that the regulatory effect of HRAS signaling on TSG101 was present not only in T29H cells, but also in other naturally occurring human ovarian cancer cells.

EXAMPLE 14

HRAS Regulates TSG101 Through p14$^{ARF}$/HDM2

After ascertaining the connection between oncogene RAS activity and the cellular levels of TSG101, it was imperative to establish the molecular mechanism by which HRAS posttranscriptionally regulated TSG101. It has been suggested that the oncoprotein MDM2 can regulate the cellular level of TSG101 through a negative feedback loop (Li et al., 2001), and since it has been well-established that RAS can exert opposing effects on MDM2, induction of MDM2 transcription and activation of MDM2 inhibitor p14$^{ARF}$ via Raf/MEK/MAPK pathway (Ries et al., 2000), it was hypothesized that HRAS might regulate TSG101 levels through modulation of p14$^{ARF}$ and HDM2.

Consistent with this hypothesis, it was observed that oncogenic RAS upregulated p14$^{ARF}$ in T29H cells and this increased cellular level of p14$^{ARF}$ which can be suppressed by U0126, a specific inhibitor of the RAS down-stream target MEK (FIG. 3A). Upregulation of p14$^{ARF}$ by RAS sequestered HDM2 in the nucleus and led to a reduction of cytoplasmic HDM2 levels in T29H cells despite the fact that the total cellular levels of HDM2 were upregulated in T29H cells (FIG. 3B). The cytoplasmic levels of HDM2 were restored in cells where HRAS$^{V12}$ levels were suppressed by H1 and H2 siRNA vectors (FIG. 3B); suggesting that oncogenic RAS activity was directly responsible for the reduction of cytoplasmic HDM2. To test if decreased cytoplasmic HDM2 levels in T29H cells were indeed liable for the up-regulation of TSG101 through a negative regulatory loop as suggested, the levels of cellular TSG101 in T29H cells in response to ectopic overexpression of HDM2 were examined.

As shown in FIG. 3C, overexpression of HDM2 in T29H led to a significant decrease in TSG101 protein levels. Similar results were observed in SKOV-3 cells. Taken together, these data suggested that oncogenic RAS activated HDM2 inhibitor p14$^{ARF}$ through the RAF/MEK/MAPK signaling pathway, suppressed cellular HDM2 activity, and consequently resulted in an increase in overall cellular levels of TSG101.

EXAMPLE 15

Upregulation of TSG101 in Human Ovarian Cancer Samples

Figure 4:
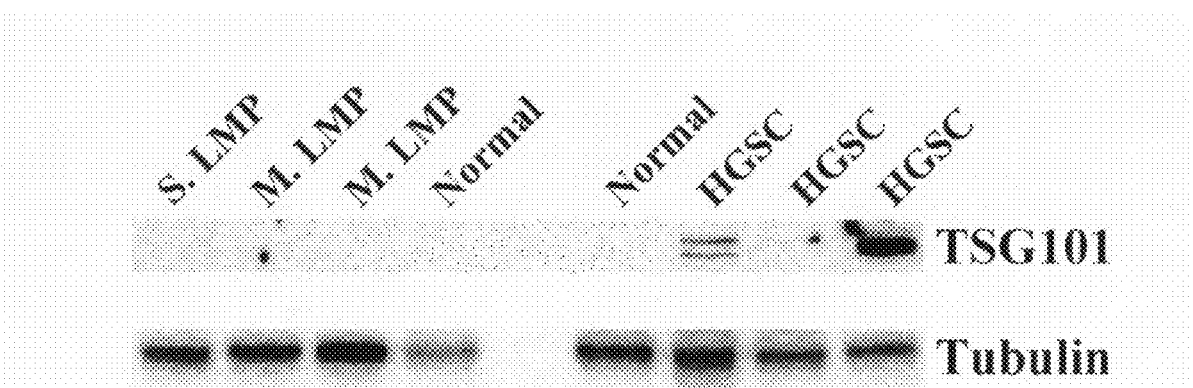
FIG. 4 shows expression levels of TSG101 in human ovarian cancers. Immunoblotting analysis showed negative expression for TSG101 in normal human ovarian tissue (lanes 4 and 6), weak to negative expression in low malignant potential ovarian tumors (lanes 1-3), and strong positive expression in high grade serous carcinomas (lanes 7-9).

To investigate the clinical association of RAS-mediated TSG101 upregulation in human ovarian surface epithelial cells, the expression levels of TSG101 in normal human ovarian and ovarian cancer samples were compared using an affinity-purified mouse anti-human TSG101 monoclonal antibody (clone 4A10) by immunoblotting analysis. While normal ovarian tissue lysates did not show significant expression for TSG101, the expression of TSG101 was increasingly positive in low grade and high grade carcinomas (FIG. 4).

EXAMPLE 16

TSG101 is Required for Growth/Survival of Ovarian Carcinoma in SKOV-3 Cells

Figure 5A:
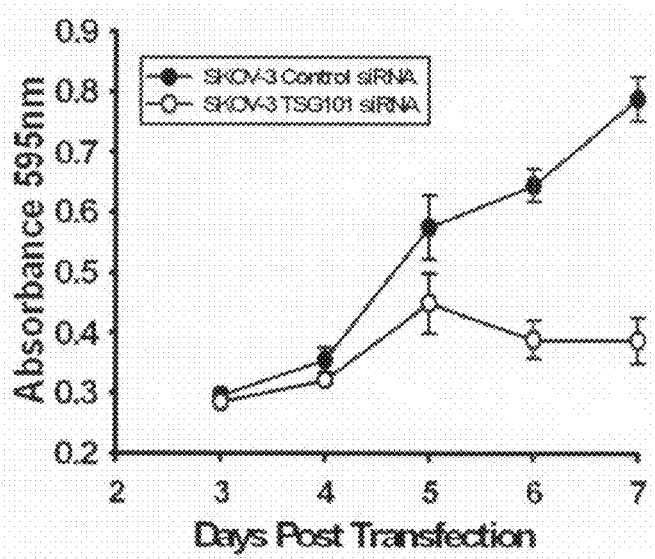
FIGS. 5A-B show effects of gene silencing of TSG101 on SKOV-3 cell viability and tumorigenicity.

To elucidate the functional role of TSG101 in ovarian cancer development, the expression of TSG101 was disrupted in SKOV-3 using a TSG101-specific siRNA duplex that have been successfully applied to suppress the expression of endogenous TSG101 in several earlier studies (Amit et al., 2004; Garrus et al., 2001; Hewitt et al., 2002; Ismaili et al., 2005). Suppression of TSG101 expression was confirmed by semi-quantitative PCR and immunoblotting. Initial observations showed no significant cellular effects in terms of rate of cell growth up to 72 hour posttransfection of TSG101 siRNA. However, when the effect of TSG101 suppression on cell viability was carefully monitored by MTT assay as a function of time, SKOV-3 cells transfected with TSG101 specific siRNA began to decrease dramatically in number beginning 5 days post transfection when compared to cells transfected with a scrambled control siRNA with the same GC content as the TSG101 siRNA (FIG. 5A). These results suggested that TSG101 was essential for the growth and survival of SKOV-3 cells.

Figure 5B:
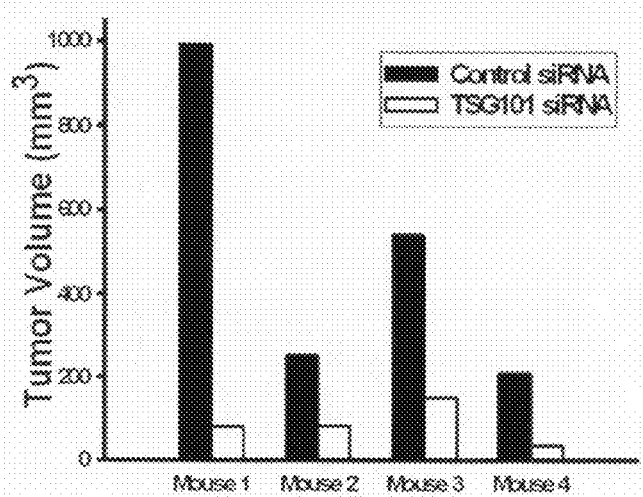

Further, in vivo tumor formation assay in nude mice was performed to determine if TSG101 knockdown affected the tumorigenicity of SKOV-3 cells. Seventy-two hours post transfection, SKOV-3 cells transfected either with TSG101 or control siRNA duplex were pair-wise injected subcutaneously into the left or right flanks, respectively, of the same BALB/c athymic nude mouse. Tumor growth was monitored for 6 weeks, at which time the tumors were harvested and tumor volume was measured. In four mice tested, tumors formed from the SKOV-3 cells treated with TSG101 siRNA were significantly smaller than tumors formed from control siRNA cells (FIG. 5B). Due to the transient nature of the siRNA duplex, the actual effect of TSG101 gene silencing should be more prominent. Taken together, these results suggested that TSG101 was important for the growth, survival, and tumorigenicity of ovarian cancer cells.

EXAMPLE 17

TSG101 Knockdown Suppresses CITED2/HIF-1α Expression and Activation

Figure 6A:
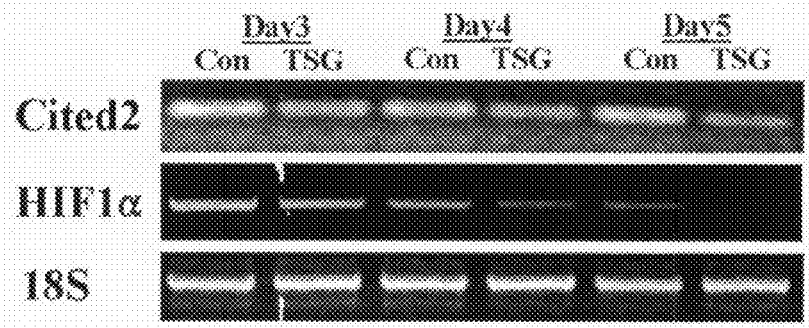
FIGS. 6A-B show regulation of cellular levels of CITED2 and HIF-1α by TSG101.
Figure 6B:
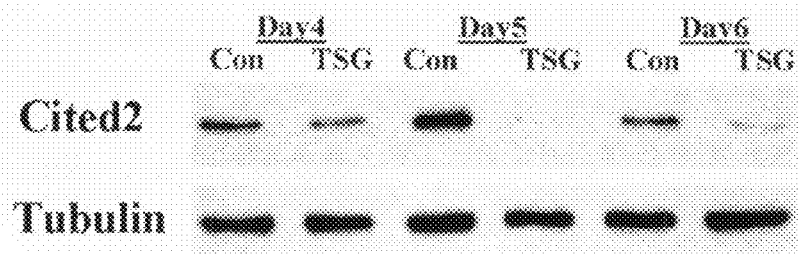

To determine the potential mechanism of TSG101 gene silencing-mediated inhibition of cell viability and tumorigenicity, the expression of a panel of genes involved in cancer formation and cell survival was examined. The expression of two closely related transcriptional regulators, the CBP/p300-interacting transactivator with ED-rich tail 2 (CITED2) and the hypoxia inducible factor-1α HIF-1α was found significantly down-regulated in SKOV-3 cells, 3 days following TSG101 siRNA transfection (FIG. 6A). Both CITED2 and HIF-1α have been implicated in regulating cell growth and survival. The decrease in CITED2 and HIF-1a messenger occurred coincidentally with the decrease of SKOV-3 cell viability on the same time scale. While the cellular protein levels of HIF-1α were too low to be detected using Western blot analysis under normoxic conditions, the cellular levels of CITED2 were significantly reduced in SKOV-3 cells with TSG101 suppressed by siRNA (FIG. 6B).

Figure 7A:
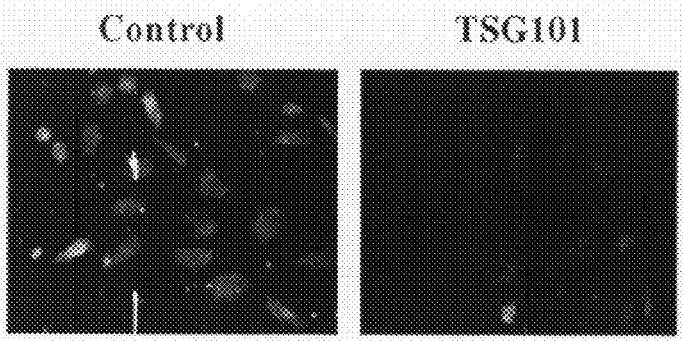
FIGS. 7A-B show regulation of HIF-1α-mediated transcriptional activation by TSG101.
Figure 7B:
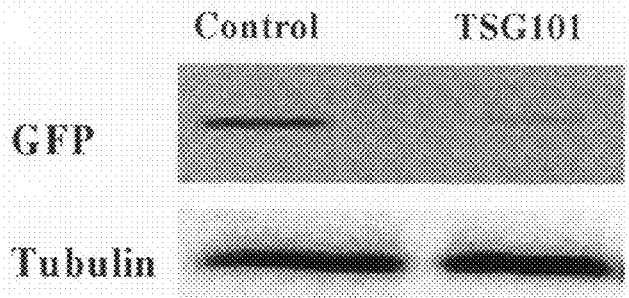

To test the functional consequence of TSG101 knockdown mediated down-regulation of CITED2/HIF-1 a HIF-1a transcriptional activity was examined using a HIF-1-inducible fluorescent reporter. This construct was created by splicing five copies of the hypoxia regulatory element (HRE) upstream of enhanced green fluorescent protein (GFP), which provided a convenient method for monitoring HIF-1 activity levels by following GFP expression using fluorescence microscopy (Moeller et al., 2004). As shown in FIG. 7A, fluorescent signal derived from GFP expression appeared significantly decreased in TSG101 knockdown cells 4 days post-transfection compared to controls. Immunoblotting analysis further confirmed a significantly decreased expression of GFP in TSG101 knock-down SKOV-3 cells (FIG. 7B).

Taken together, these results indicated that TSG101 was an important regulator of HIF-1α gene expression and transcriptional activation.

EXAMPLE 18

Patients and Specimens

Formalin-fixed, paraffin-embedded primary ovarian cancer specimens were obtained from patients who underwent surgery for primary epithelial ovarian carcinoma (EOC) at M. D. Anderson Cancer Center (MDACC). All tissue specimens were collected under Institutional Review Board-approved HIPAA-compliant protocols at MDACC and were classified according to WHO criteria.

EXAMPLE 19

Construction of Tissue Microarrays

Tissue blocks were constructed as previously described (Rosen et al., 2004). The final tissue microarray consisted of 2 blocks. All samples were spaced 0.5 mm apart. Five-micrometer sections were obtained from the microarray and stained with hematoxylin and eosin to confirm the presence of tumor and to assess the tumor histology. Tumor samples were randomly arranged on the blocks. The first tissue microarray block was constructed to analyze under the same conditions 5 normal ovaries, 7 serous low malignant potential tumors, 7 mucinous low malignant tumors, 10 low grade serous carcinomas, 19 high grade serous carcinomas, 5 low grade, 7 high grade endometrioid carcinomas and 6 clear cell carcinomas. The second tissue microarray contains duplicates of 422 cases of primary ovarian carcinoma. The array was read according to the given tissue microarray map; each core was scored individually and the results were presented as the mean of the two replicate core samples. Cases in which no tumor was found or no cores were available were excluded from the final data analysis.

EXAMPLE 20

Immunohistochemical Analysis

The tissue microarray slides were subjected to immunohistochemical staining as follows. After initial de-paraffinization, endogenous peroxidase activity was blocked by using 0.3% hydrogen peroxide. De-paraffinized sections were microwaved in 10 mM citrate buffer (pH 6.0) to unmask the epitopes. The slides were then incubated at 4° C. overnight against TSG101 (1:100, Clone 4A10, Novus Biologicals, Littleton, Colo.) and p21WAF1/CIP1 (1:50, Neomarkers, Fremont, Calif.) next with biotin-labeled secondary antibody for 20 minutes, and finally with a 1:40 solution of streptavidin:peroxidase for 20 minutes (Biocare medical, Walnut Creek, Calif.). Tissues were then stained for 5 minutes with 0.05% 3',3-diaminobenzidine tetrahydrochloride that had been freshly prepared in 0.05 M Tris buffer at pH 7.6 containing 0.024% $H_2O_2$ and then counterstained with hematoxylin, dehydrated, and mounted. All of the dilutions of antibody, biotin-labeled secondary antibody, and streptavidin-peroxidase were made in phosphate-buffered saline (PBS, pH 7.4) containing 1% bovine serum albumin. Negative controls were made by replacing the primary antibody with phosphate-buffered saline.

All controls gave satisfactory results. Immunostaining for TSG101 was analyzed by computerized automated image analysis (Ariol SL-50, Applied imaging, San Jose, Calif.). Quantitation was done on the whole core tissue at 20° C., considering only tumor epithelial cells by appropriate training of the computerized system. Cytoplasmic immunostaining for TSG101 was measured as the total integrated optical density and expressed in arbitrary optic density units. For statistical analysis, all cases displaying total integrated optical density (mean±SE) were then group together in a 0-3 scale. Negative staining (score 0) was defined as the total absence of marker (brown color). The mean of the results from the two replicate core samples from each tumor specimen was considered for each case. Counting criteria and software settings were identical for all slides. Quantitation was done blinded to clinicopathological information. Normal ovarian epithelial cells were used as a comparison for intensity and pattern of staining.

For statistical analysis cases exhibiting negative and low expression (score 1) were grouped as "low" expressors and those expressing moderate (score 2) or strong (score 3) as "High" expressors. For p21WAF1/CIP1 a positive nuclear area above 2% was considered overexpression and below 2% as low expression.

EXAMPLE 21

Statistical Analysis

Descriptive statistics were calculated; Spearman Rank Correlation Methods were used to estimate the pair-wised associations of three markers; Chi-square Tests, or if there were 5 or fewer observations in a cell, Fisher's Exact Tests were performed to assess the association between two categorical variables; Wilcoxon Rank Sum non-parametric methods were used to assess the association between TSG101 and clinical variables and between p21 and clinical variables. All P-values presented were two sided. Kaplan-meier method was for survival analysis. All statistic analyses were carried out in SAS 8.0 or Splus 6.1 or StatXact 4, as appropriate. Results were considered statistically significant at the p<0.05 level.

EXAMPLE 22

Flow Cytometry Analysis

SKOV-3 cells transfected with either TSG101 or control siRNA were grown and harvested 4 and 6 days after transfection. $1 \times 10^6$ cells were trypsinized from 10 cm plates and transferred to FACS tubes, washed twice with PBS, and then fixed with 70% ethanol for 2 h on ice. Ethanol was removed by centrifugation and cells were rehydrated in PBS at room temperature for 5 min. Cells were centrifuged to remove PBS and stained with 1 ml of propidium iodide staining solution (0.1% Triton X-100, 0.2 mg/ml RNAase A, 0.05 mg/ml propidium iodide, prepared fresh) for 1 h at room temperature. Cellular DNA content was then determined on a Becton-Dickinson FACS-Scan apparatus.

EXAMPLE 23

Nuclear DNA Condensation Staining $2$-$3 \times 10^5$ SKOV-3 cells were plated in 3 cm tissue culture plates containing polylysine coated coverslips, and transfected with either control or TSG101 siRNA. Cells on coverslips were stained 5 days post-transfection with Hoechst 22658 for 30 min, rinsed with PBS, and sealed onto glass slides. Nuclear DNA condensation was examined using a fluorescence microscope (Olympus BX51) equipped with a Hamamatsu digital camera (C4742-95).

EXAMPLE 24

Caspase Activity Assays

SKOV-3 cells transfected with either control or TSG101 siRNA were grown in 10 cm plates to 70-80% confluence, then harvested by trypsinization, washed twice in PBS and once in wash buffer (100 mM HEPES pH 7.4, 0.5 mM EDTA, 1 mM DTT, 0.1 mM PMSF, 2 µg/ml leupeptin, 2 µg/ml pepstatin). The cells were lysed on ice for 30 min with frequent vortexing in 150 µl of lysis buffer (wash buffer plus 1% Triton-X100). Cell debris was removed by centrifugation at 16,000 g for 20 min at 4° C. Lysate protein concentration was determined by Bradford assay (Bio-Rad). Caspase 3 activity was measured using fluorogenic substrates DEVE-AFC that is specific for caspase 3. Release of free AFC was monitored using a Fluoroskan fluorescence microplate reader with excitation and emission set to 405 and 510 nm, correspondingly.

EXAMPLE 25

Gene Expression Analysis

Total RNA was isolated from cells using Trizol reagent (Invitrogen), and concentration was determined by absorbance at 260 nm. Semiquantitative RT-PCR was carried out using 1 µg of isolated total RNA. Primers used for RT-PCR were TSG101 forward 5'-TCCAGTCTTCTCTCGTC-CTATTTC-3' (SEQ ID NO: 1), reverse 5'-TTTCCTCCT-TCATCCGCCATCTC-3' (SEQ ID NO:2), p21 forward 5'-CGACTGTGATGCGCTAATGG-3' (SEQ ID NO: 9), reverse 5'-CCGTTTTCGACCCTGAGAG-3' (SEQ ID NO:10).

EXAMPLE 26

Immunoblotting Analysis

Cells transfected with either control or TSG101 siRNA were passaged and subsequently harvested on the appropriate days by trypsinizing cells, washing pelleted cells in PBS and then lysing cells in SDS lysis buffer. Protein concentration of cell lysates was assayed with the Bio-Rad protein assay reagent. Equal amounts of protein (10-20 µg) were loaded onto 12% SDS polyacrylamide mini-gels (Bio-Rad) or 10% Tricine-SDS gels and transferred to PVDF membranes. PVDF blots and the remaining polyacrylamide gels were stained with Ponceau S and Coomassie Blue, respectively, to ensure equal loading and even transfer of the samples. After being blocked overnight in 5% milk in TBS-Tween, blots were incubated with p21 antibody (1:2000 Cell Signaling, Danvers, Mass.) or TSG101 (1:2000) for 1.5 h at room temperature, followed by incubation in anti-mouse IgG secondary antibody (1:2000, Bio-Rad, Hercules, Calif.). Immunoblots were developed by enhanced chemiluminescence (Pierce, Rockford, Ill.).

EXAMPLE 27

Chromatin Immunoprecipitation (ChIP) Assays

Chromatin immunoprecipitation kits from Upstate Cell Signaling (Charlottesville, Va.) were used according to manufacturers instruction with minor modifications. Briefly, SKOV-3 cells transfected with control or TSG101 siRNA were grown to $1 \times 10^6$ cells in 10 cm plates. DNA binding proteins were crosslinked by adding 1% formaldehyde to culture media and incubating at 37° C. for 10 min. Cells were washed with PBS, scraped off from plates in ice cold PBS with protease inhibitors, and harvested by centrifugation at 300 g. Cell pellets were lysed in SDS lysis buffer (1% SDS, 10 mM EDTA, 50 mM Tris, pH 8.1) on ice for 10 min, then divided into 200 µl aliquots and sonicated according to pre-determined optimized conditions to shear genomic DNA. After shearing, sonicates were diluted 10 fold in ChIP dilution buffer (0.01% SDS, 1.1% Triton X-100, 2 mM EDTA, 20 mM Tris-HCl, 500 mM NaCl, pH 8.1). A small portion of the lysate was retained at this point to be used in determining the amount of total DNA in each sample.

Lysates were then precleared by incubation with a Protein A agarose bead slurry for 2 h at 4° C. under rotation. Protein A beads were removed by centrifugation and lysates were then incubated with TSG101 antibody (10 μg, Novus, IgG isotype) at 4° C. overnight with continuous rotation. Following overnight antibody incubation, Protein A agarose beads were added to the lysate antibody mix and incubated for 2 h at 4° C. with continuous rotation. Supernatant was then removed and the bead slurry washed once with 1 ml of each buffer in succession; low salt buffer (0.1% SDS, 1% Triton X-100, 2 mM EDTA, 20 mM Tris-HCl, 150 mM NaCl, pH 8.1), high salt buffer (low salt buffer with 500 mM NaCl), lithium chloride buffer (0.25 M LiCl, 1% IGEPAL-CA630, 1% deoxycholic acid, 1 mM EDTA, 10 mM Tris, pH 8.1), and twice with 1 ml TE buffer (10 mM Tris-HCl, 1 mM EDTA, pH 8.1). Protein DNA complex was eluted with two volumes of 250 μl elution buffer at room temperature with shaking for 15 min. Crosslinking was reversed by the addition of 20 μl 5 M NaCl and incubation at 65° C. for 4 hours. Reaction was stopped by the addition of 10 μl 0.5 M EDTA, and proteins were digested with Proteinase K (2 μl of 10 mg/ml stock) for 1 h at 45° C. DNA was recovered by phenol/chloroform extraction and ethanol precipitation. Pelleted DNA was resuspended in TBE. PCR was performed using the following primers for the p21 promoter, forward 5'-CGTGGTGGTG-GTGAGCTAGA-3' (SEQ ID NO: 11), reverse 5'-CTGTCT-GCACCTTCGCTCCT-3' (SEQ ID NO:12).

EXAMPLE 28

Upregulation of TSG101 in Human Ovarian Cancer Samples

To investigate the clinical implication of RAS-mediated TSG101 upregulation in human ovarian surface epithelial cells, the expression levels of TSG101 in ovarian carcinomas was probed using human ovarian cancer tissue arrays. An affinity-purified mouse anti-human TSG101 monoclonal antibody (clone 4A10) that specifically recognizes a single protein band (TSG101 protein molecular mass, 46 kDa) in whole-cell lysates by Western blot analysis was used. This antibody has been successfully used for immunohistochemical staining (Zhong et al., 1997; Zhong et al., 1998). Overall, localization of the TSG101 was mostly found in the cytoplasmic compartment of epithelial cells. While normal ovarian epithelial cells did not show significant expression for TSG101 (FIG. 9A), the expression of TSG101 was increasingly positive in borderline tumors, low grade and high grade carcinomas compared to normal ovarian surface epithelial (FIG. 9).

In one case, containing a transition zone between normal ovarian surface epithelial and a high grade serous carcinoma, it was observed that normal ovarian surface epithelial was negative while the tumor showed strong cytoplasmic staining for TSG101 (FIG. 9B). Similar findings were observed in a mucinous LMP tumor where an area of mucinous cystadenoma weakly expressed the marker compared to the adjacent LMP lesion (FIG. 9D). The levels of expression for TSG101 varied among ovarian carcinomas showing a wide range of variability from totally negative (26.3%) to strongly positive (23%) with over 70% samples showing certain degrees of TSG101 up-regulation (FIG. 9G).

EXAMPLE 29

Prognostic Value of Tsg101 Expression Levels in EOC

Figure 10:
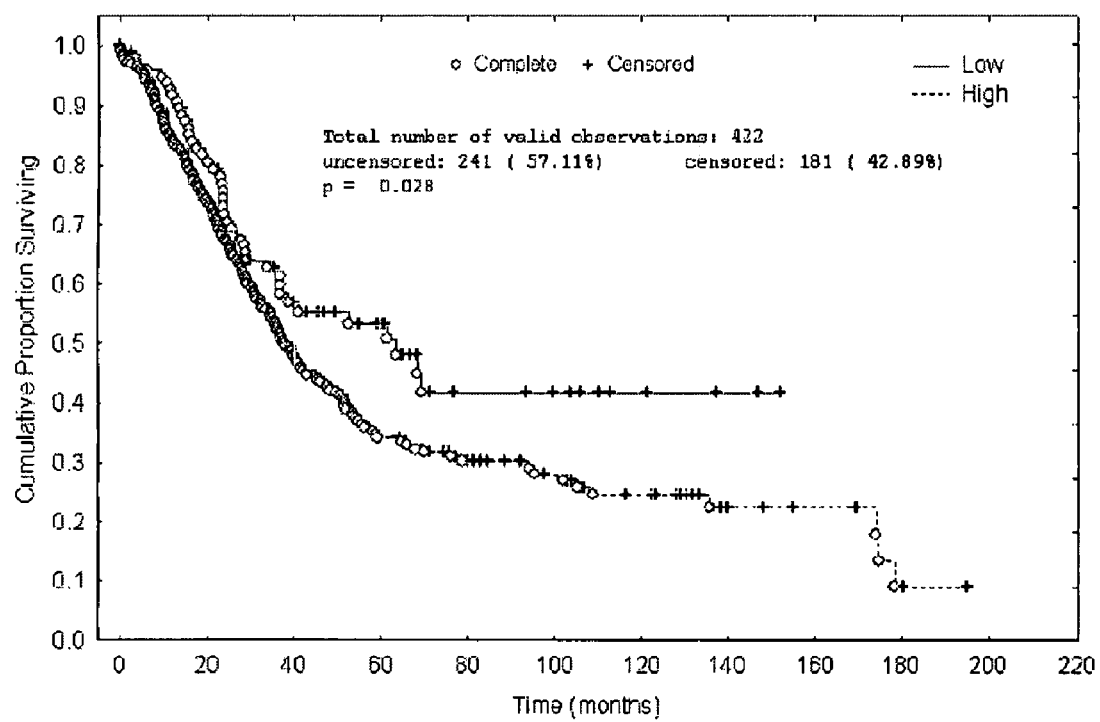
FIG. 10 shows prognostic significance of TSG101 expression levels in ovarian carcinomas. Kaplan-Meier survival curves for ovarian cancer patients with either high or low TSG101 expression are shown.

As shown in Table 1, tumor histotype was most frequently upregulated in serous carcinoma, poorly differentiated carcinomas and malignant mixed mullerian tumors than the other histotypes. Patients with grade 3 ovarian cancer had a significantly higher percentage of high TSG101 as compared with patients with grade 1 or grade 2 and patients with stage 3 or stage 4 had a significantly higher percentage of high TSG101 as compared with patients with stage 1 or stage 2. Furthermore, suboptimal cytoreduction was significantly correlated with high TSG101 (p<0.014), while no significant difference was observed in patient's age at the time of diagnosis between high and low TSG101 levels. The impact of high TSG101 concentration on ovarian cancer survival was investigated. Kaplan-Meier survival curves for ovarian cancer patients with either low or high TSG101 level revealed that patients with low expression of TSG101 survive longer than those with high expression of TSG101 (FIG. 10).

TABLE 1

Chi-square Test or Fisher's exact test to assess the association between Tsg101 (score) and clinical variables

| Clinical Variables | TSG101 scores | | P-value |
|---|---|---|---|
| | Low | High | |
| Age | | | |
| <=55 | 39 (25.32%) | 115 (74.68%) | 0.81 |
| >55 | 65 (24.25%) | 203 (75.75%) | |
| Histotype | | | 0.0083 |
| Clear cell carcinoma | 6 (40%) | 9 (60%) | |
| Endometroid adenocarcinoma | 19 (45.24%) | 23 (54.76%) | |
| MMMT | 4 (26.67%) | 11 (73.33%) | |
| Mucinous adenoarcinoma | 3 (50%) | 3 (50%) | |
| Poorly differentiated carcinoma | | | |
| Serous carcinoma | 68 (21.18%) | 253 (78.81%) | |
| Transitional cell carcinoma | 0 (0%) | 7 (100%) | |
| Grade | | | 0.044 |
| 1 | 8 (34.78%) | 15 (65.22%) | |
| 2 | 10 (43.48%) | 13 (56.52%) | |
| 3 | 87 (22.96%) | 292 (77.04%) | |
| Stage | | | 0.027 |
| I | 11 (30.56%) | 25 (69.44%) | |
| II | 15 (45.45%) | 18 (54.55%) | |
| III | 60 (22.30%) | 209 (77.70%) | |
| IV | 19 (22.89%) | 64 (77.11%) | |
| Type of cytoreduction | | | 0.014 |
| No surgery | 0 (0%) | 1 (100%) | |
| Optimal | 71 (33.81%) | 139 (66.19%) | |
| Suboptimal | 32 (21.05%) | 120 (78.95%) | |

EXAMPLE 30

Suppression of TSG101 in Ovarian Cancer Epithelial Cells Results in Growth Inhibition Cell Cycle Arrest and Apoptosis The potential mechanisms by which increased levels of TSG101 contributed to development and progression of EOC were examined by disrupting the expression of TSG101 in SKOV-3 using a TSG101-specific siRNA that had been successfully applied to suppress the expression of endogenous TSG101 (Hewitt et al., 2002; Amit et al., 2004; Garrus et al., 2001).

Suppression of TSG101 expression was confirmed by semiquantitative PCR and immunoblotting (FIG. 11A). Initial observations showed no significant cellular effects on cell growth up to 72 h posttransfection with TSG101 siRNA.

However, when the effect of TSG101 suppression on cell growth was carefully monitored as a function of time, the SKOV-3 cells transfected with TSG101 specific siRNA started to decrease dramatically in number beginning 5 days post transfection when compared to cells transfected with a scrambled control siRNA with the same GC content as the TSG101 siRNA (FIG. 11B).

To further examine the potential mechanism of TSG101 suppression mediated cell growth inhibition, flow cytometric cell cycle analyses of SKOV-3 cells transfected either with TSG101 or control siRNA at days 4 and 6 were performed. On day 4, cellular DNA content of both TSG101 and Control siRNA transfected cells was very similar (FIG. 11C), while on day 6, TSG101 cells exhibited a significant increase in the number of cells in G2/M phase and a decrease in G1/G0 phase cells, indicating a block in the cell cycle at G2/M phase (FIG. 11D). Moreover, a significant population of sub-G1 apoptotic cell debris was observed on day 6 but was not seen on Day 4. These observations were further collaborated by the apparent increases in both nuclear DNA condensation/fragmentation (FIG. 11E) and caspase 3 activity (FIG. 11F) in TSG101 knockdown cells. Taken together, these results suggested that silencing of TSG101 resulted in G2/M arrest and subsequently cell death in SKOV-3 cells.

EXAMPLE 31

Suppressing Tsg101 Promotes p21 Expression and Activation

Figure 12A:
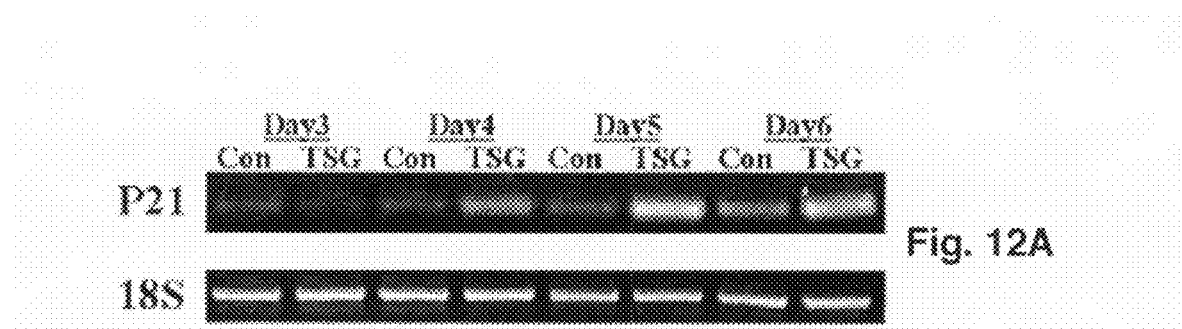
FIGS. 12A-D show regulation of P21 by TSG101.
Figure 12B:
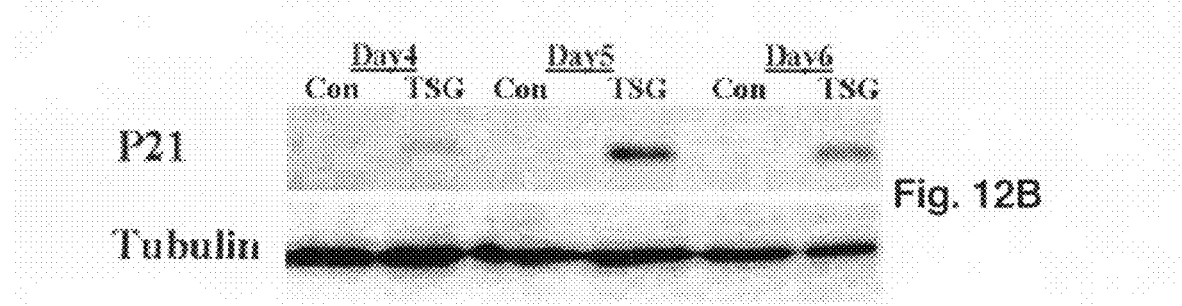
Figure 12C:
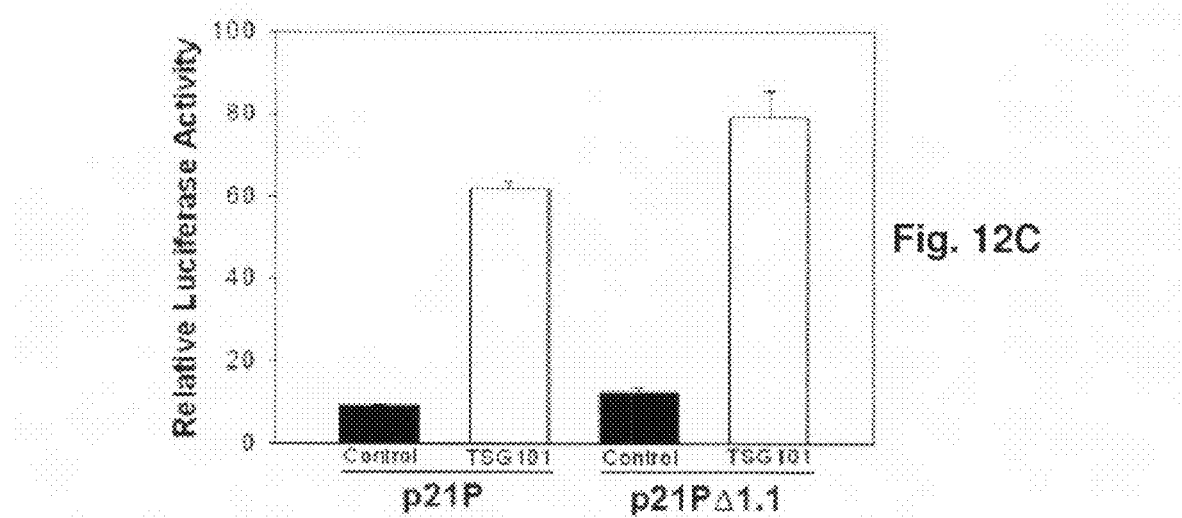
Figure 12D:
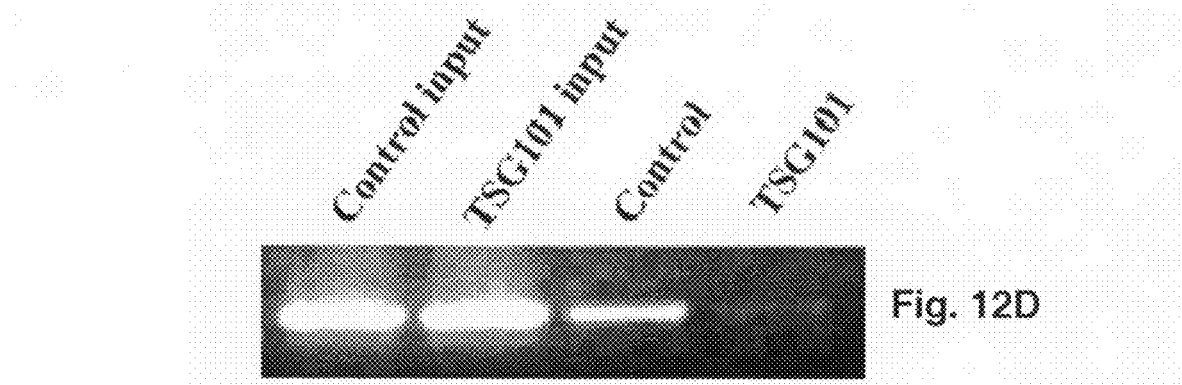

To determine the molecular mechanism of TSG101 gene silencing-mediated cell cycle arrest and inhibition of cell viability, the expression of a panel of genes involved in controlling cell cycle progression and cell survival was examined. The expression of one important tumor suppressor, the cyclin-dependent kinase inhibitor p21, was found significantly upregulated both at the messenger RNA and protein levels in SKOV-3 cells with reduced TSG101 (FIGS. 12A & 12B). The increase in p21 induced by TSG101 silencing occurred after 4 days following siRNA transfection, concurrent with the aforementioned cell cycle arrest and decrease of viability in SKOV-3 cells.

To investigate the mechanism by which TSG101 silencing induced the accumulation of p21 mRNA, a plasmid construct, p21P, with a luciferase reporter gene under the transcriptional control of the p21 promoter was co-transfected into the SKOV-3 cells either with TSG101 specific or control siRNA. As shown in FIG. 13A, luciferase activity was significantly increased in TSG101 knockdown cells compared to controls, suggesting that TSG101 silencing-induced p21 mRNA accumulation was partly due to a transcriptional activation of the p21 gene. Since SKOV-3 cells are p53-null, this apparent TSG101 silencing-mediated transcriptional activation of p21 was most likely p53-independent.

To further confirm this observation, the luciferase reporter activity was monitored using a deletion p21 reporter construct, p21PΔ1.1, which contained a 1.1 kb deletion that removed the consensus p53-responsive element from the 5' region of the 2.4 kb p21 promoter 27. As shown in FIG. 13A, the full-length p21 promoter construct and p53-deletion construct responded to TSG101 silencing to similar extents, both leading to a 6 fold induction of p21. Taken together, these data suggested that suppression of TSG101 in ovarian cancer cells led to a p53-independent transcriptional activation of p21. Since TSG101 contained a putative DNA-binding domain and could act as a general transcriptional suppressor 2, it was hypothesized that TSG101, acting as a transcriptional corepressor, suppressed the transactional activation of p21 by binding to the p21 promoter. Consequently, suppression of TSG101 by siRNA led to the transcriptional activation of p21.

To test this hypothesis, a chromatin immunoprecipitation assay using TSG101 specific antibody was performed. To monitor specifically TSG101 recruitment to the p21 promoter, primers to amplify the p21 promoter were designed, and the amount of p21 DNA immunoprecipitated by TSG101 antibody was measured. The association of TSG101 with p21 promoter was apparent in SKOV-3 cells treated with control siRNA and the recruitment of TSG101 to this promoter was dramatically reduced in TSG101 knockdown SKOV-3 cells (FIG. 13B). These results provided the first biochemical evidence of TSG101 recruitment to the p21 promoter and demonstrated that reduced TSG101 binding to the p21 promoter in TSG101 knockdown SKOV-3 cells was responsible for the induction of p21 expression.

EXAMPLE 32

Association Between TSG101 and p21 in Ovarian Carcinomas

Based on the causal relationship between TSG101 and p21 observed in ovarian cancer cells, whether a pair-wised association between TSG101 and p21 existed in ovarian carcinomas was determined. Spearman Rank Correlation analysis revealed that markers TSG101 and p21 were significantly correlated with spearman rank correlation –0.11 and p value 0.04. In addition, Chi-square Test was performed to assess the association between TSG101 and p21. As shown in Table 2, TSG101 was significantly associated with p21. Patients with lower TSG101 score had a significantly higher rate of high p21 score. Taken together, these results confirmed the prediction based on the in vitro mechanistic study that there was a significant negative correlation between the markers TSG101 and p21 in human ovarian carcinomas.

TABLE 2

Chi-square test to asses the association between TSG101 and p21

|  |  | p21 | | P-value |
|---|---|---|---|---|
|  |  | <2% | >2% |  |
| TSG101 | Low | 24 (23.76%) | 77 (76.24%) | 0.016 |
|  | High | 82 (37.44%) | 137 (62.56%) |  |

The following references were cited herein:
Amit I et al., 2004, Genes Dev. 18:1737-1752.
Anttila, M. A. et al., 1999, Br J Cancer 79: 1870-1878.
Bennett N. A. et al., 2001, Cell Mol. Biol. (Noisy.-le-grand) 47:1187-1193.
Berchuck, A. and M. Carney, 1997, Biochem. Pharmacol. 54:541-544.
Blum, H. et al., 1987, Electrophoresis 8:93-99.
Blum, R et al., 2005, Cancer Res. 65:999-1006.
Carstens, M. J et al., 2004, J. Biol. Chem. 279:35984-35994.
Elbendary A. et al., 1994, Cell Growth Differ 5:1301-1307.
el Deiry W. S. et al., 1993, Cell 75: 817-825.
el Diery W. S. et al., 1994, Cancer Res 54: 1169-1174.
Feig, L. A et al., 1996, Trends Biochem. Sci. 21:438-441.
Feng, G. H. et al., 2000, Cancer Res. 60:1736-1741.
Garrus, J. E et al., 2001, Cell 107:55-65.
Gayther, S. A. et al., 1997, Oncogene 15:2119-2126.
Hancock, J. F. et al., 1990, Cell 63:133-139.
Harper J. W. et al., 1993, Cell 75: 805-816.
Hewitt, E. W. et al., 2002, EMBO J. 21:2418-2429.
Ismaili, N. et al., 2005, J. Biol. Chem. 280:11120-11126.
Nichieli P. et al., 1994, Cancer Res 54:3391-3394.

Kauffmann-Zeh, A., P. et al., 1997, Nature 385:544-548.
Khosravi-Far, R., et al., 1996, Mol. Cell Biol. 16:3923-3933.
Koon, N., R. et al., 2004, Gut 53:235-240.
Kranc, K. R., et al., 2003, Mol. Cell Biol. 23:7658-7666.
Krempler, A., et al. 2002, J. Biol. Chem. 277:43216-43223.
Lee, M. P. and A. P. Feinberg, 1997, Cancer Res. 57:3131-3134.
Li, L. and S. N. Cohen, 1996, Cell 85:319-329.
Li, L., et al., 1998, Cell 93:
Li, L., et al. 1997. Cell 88:143-154.
Li, L., et al., 2001. Proc. Natl. Acad. Sci. U.S.A 98:1619-1624.
Lim, J. H., et al., 2004., Oncogene 23:9427-9431.
Liu, J., G. et al., 2004. Cancer Res. 64:1655-1663.
Liu, R. T., et al., 2002. Oncogene 21:4830-4837.
Marshall, C. J. 1995, Cell 80:179-185.
Mazure, N. M., et al., 2004, Biochem. Pharmacol. 68:971-980.
Mei, F. C., et al., 2005, FASEB J. 05-4586fje.
Moeller, B. J. et al., 2004, Cancer Cell 5:429-441.
Oh, H et al., 2002, Proc Natl Acad Sci U.S.A 99: 5430-5435.
Palmero, I., et al., 1998. Nature 395:125-126.
Pennacchietti, S., et al., 2003, Cancer Cell 3:347-361.
Ries, S., et al., 2000, Cell 103:321-330.
Rosen D. G et al., 2004, Mol Pathol 17: 790-797.
Ruland, J., et al., 2001, Proc. Natl. Acad. Sci. U.S.A 98:1859-1864.
Ryan, H. E., et al., 2000, Cancer Res. 60:4010-4015.
Semenza, G. L., 2003, Nat. Rev. Cancer 3:721-732.
Sheikh, M. S. et al., 1994, Oncogene 9: 3407-3415.
Shevchenko, A., et al., 1996, Anal. Chem. 68:850-858.
Shibatohge, M., et al., 1998, J. Biol. Chem. 273:6218-6222.
Shih, I. and R. J. Kurman. 2004, Am. J. Pathol. 164:1511-1518.
Steiner, P., et al., 1997, Nat. Genet. 16:332-333.
Sun, H. B., et al., 1998, Proc. Natl. Acad. Sci. U.S.A 95:13555-13560.
Sun, Z., et al., 1997, Oncogene 15:3121-3125.
Tien, E. S., et al., 2004, J. Biol. Chem. 279:24053-24063.
Vavvas, D., X. et al., 1998. J. Biol. Chem. 273:5439-5442.
Wagner, K. U., et al., 1998. Oncogene 17:2761-2770.
Wagner, K. U., et al., 2003. Mol. Cell Biol. 23:150-162.
Wang, Q., et al., 1998, Oncogene 16:677-679.
Watari, Y., et al., 1998. Gene 224:53-58.
Yang, G., et al., 2003, Oncogene 22:5694-5701.
Yang, Z. F., et al., 2004, Cancer Res. 64:5496-5503.
Yin, Z., et al., 2002. Proc. Natl. Acad. Sci. U.S.A 99:10488-10493.
Young, T., et al., 2005. Oncogene 24:6174-6184.
Young, T. W., et al., 2004. Cancer Res. 64:4577-4584.
Zhang W. et al., 1995, Cancer Res 55: 668-674
Zhong Q et al., 1997, Cancer Res 57: 4225-4228.
Zhong Q et al., 1998, Cancer Res 58: 2699-2702.
Zhu, G., R. et al., 2004, Int. J. Cancer 109:541-547.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

---

What is claimed is:

1. A method of diagnosing cancer in an individual, comprising:
    obtaining a biological sample from the individual; and
    detecting tumor susceptibility gene 101 (TSG101) in the sample, wherein the overexpression of the TSG101 either alone or in combination with presence of other markers characteristic of the cancer in the sample is indicative of presence of cancer in the individual; wherein said cancer is one of ovarian cancer, breast cancer, prostate cancer, cervical cancer, lung cancer or pancreatic cancer.

2. The method of claim 1, wherein the biological sample is tumor tissue biopsy, fine needle aspiration biopsy, whole blood, serum, or plasma.

3. The method of claim 1, wherein the TSG101 is detected by Northern blot, western blot, PCR, dot blot, Elisa sandwich assay, radioimmunoassay, DNA array chips, flow cytometry, SELDI-TOF, mass spectrometry, protein array or other proteomic assays.

4. The method of claim 1, wherein said cancer exhibits overexpression of TSG101, overexpression/mutation of RAS, underexpression/mutation of p21 or a combination thereof.

5. The method of claim 1, wherein the markers characteristic of the cancer are CA 125 (ovarian cancer), CA 15-3 and 27-29 (breast cancer), CEA; Carcinogenic Embryonic Antigen (colon, lung, breast, pancreas, and gastrointestinal tract cancers), PSA (prostate cancer), AFP; .alpha.-fetoprotein (liver cancer), CA 19-9 or CEACAM 1 (pancreatic cancer).

6. The method of claim 1, wherein said individual is suspected of suffering from cancer or is at risk of developing cancer.

7. A method of determining the prognosis of a cancer patient, comprising: obtaining a biological sample from the patient; and detecting TSG101 in sample, wherein overexpression of TSG101 either alone or in combination with presence of other markers characteristic of the cancer; wherein said cancer is one of ovarian cancer, breast cancer, prostate cancer, cervical cancer, liver cancer, lung cancer or pancreatic cancer indicates that the patient would have a poor prognosis.

8. The method of claim 7, wherein the biological sample is tumor tissue biopsy, fine needle aspiration biopsy, whole blood, serum, or plasma.

9. The method of claim 7, wherein the TSG101 is detected by Northern blot, western blot, PCR, dot blot, Elisa sandwich assay, radioimmunoassay, DNA array chips and flow cytometry, SELDI-TOF, mass spectrometry, protein array or other proteomic assays.

10. The method of claim 7, wherein said cancer exhibits overexpression of TSG101, overexpression/mutation of RAS, underexpression/mutation of p21 or a combination thereof.

11. The method of claim 7, wherein the markers characteristic of the cancer are CA 125 (ovarian cancer), CA 15-3 and 27-29 (breast cancer), CEA; Carcinogenic Embryonic Antigen (colon, lung, breast, pancreas, and gastrointestinal tract cancers), PSA (prostate cancer), AFP; .alpha.-fetoprotein (liver cancer), CA 19-9 and CEACAM 1 (pancreatic cancer).

* * * * *

SEQUENCE LISTING

```
<160> NUMBER OF SEQ ID NOS: 12

<210> SEQ ID NO 1
<211> LENGTH: 24
<212> TYPE: DNA
<213> ORGANISM: artificial sequence
<220> FEATURE:
<223> OTHER INFORMATION: Forward primer for Tumor Susceptibility
      Gene (TSG101)

<400> SEQUENCE: 1
tccagtcttc tctcgtccta tttc                                            24

<210> SEQ ID NO 2
<211> LENGTH: 23
<212> TYPE: DNA
<213> ORGANISM: artificial sequence
<220> FEATURE:
<223> OTHER INFORMATION: Reverse primer for Tumor Susceptibility
      Gene (TSG101)

<400> SEQUENCE: 2
tttcctcctt catccgccat ctc                                             23

<210> SEQ ID NO 3
<211> LENGTH: 20
<212> TYPE: DNA
<213> ORGANISM: artificial sequence
<220> FEATURE:
<223> OTHER INFORMATION: Forward primer for CBP/p300
      interacting transactivator
      with ED rich tail 2 (CITED2)

<400> SEQUENCE: 3
```
ggcggctctg gcagcagctc                                              20

<210> SEQ ID NO 4
<211> LENGTH: 20
<212> TYPE: DNA
<213> ORGANISM: artificial sequence
<220> FEATURE:
<223> OTHER INFORMATION: Reverse primer for CBP/p300
      interacting transactivator
      with ED rich tail 2 (CITED2)

<400> SEQUENCE: 4
cgggcagctc cttgatgcgg                                              20

<210> SEQ ID NO 5
<211> LENGTH: 22
<212> TYPE: DNA
<213> ORGANISM: artificial sequence
<220> FEATURE:
<223> OTHER INFORMATION: Forward primer for Hypoxia
      Inducible Factor-1 alpha (HIF-1 alpha)

<400> SEQUENCE: 5
cctgcactca atcaagaatt gc                                           22

<210> SEQ ID NO 6
<211> LENGTH: 23
<212> TYPE: DNA
<213> ORGANISM: artificial sequence
<220> FEATURE:
<223> OTHER INFORMATION: Reverse primer for Hypoxia
      Inducible Factor-1 alpha (HIF-1 alpha)

<400> SEQUENCE: 6
ttcctgctct gtttggtgag gct                                          23

<210> SEQ ID NO 7
<211> LENGTH: 21
<212> TYPE: DNA
<213> ORGANISM: artificial sequence
<220> FEATURE:
<223> OTHER INFORMATION: Sense Strand for TSG101 siRNA;
      where t at positions 19 and 20
      are dideoxy-thymidine

<400> SEQUENCE: 7
ccuccagucu ucucucguct t                                            21

<210> SEQ ID NO 8
<211> LENGTH: 21
<212> TYPE: DNA
<213> ORGANISM: artificial sequence
<220> FEATURE:
<223> OTHER INFORMATION: Antisense for TSG101 siRNA;
      where t at positions 1 and 2
      are dideoxy-thymidine

<400> SEQUENCE: 8
ttggagguca gaagagagca g                                            21

<210> SEQ ID NO 9
<211> LENGTH: 20
<212> TYPE: DNA
<213> ORGANISM: artificial sequence
<220> FEATURE:
<223> OTHER INFORMATION: Forward primer for P21

<400> SEQUENCE: 9

-continued

```
cgactgtgat gcgctaatgg                                                    20

<210> SEQ ID NO 10
<211> LENGTH: 19
<212> TYPE: DNA
<213> ORGANISM: artificial sequence
<220> FEATURE:
<223> OTHER INFORMATION: Reverse primer for P21

<400> SEQUENCE: 10
ccgttttcga ccctgagag                                                     19

<210> SEQ ID NO 11
<211> LENGTH: 20
<212> TYPE: DNA
<213> ORGANISM: artificial sequence
<220> FEATURE:
<223> OTHER INFORMATION: Forward primer for P21 promoter

<400> SEQUENCE: 11
cgtggtggtg gtgagctaga                                                    20

<210> SEQ ID NO 12
<211> LENGTH: 20
<212> TYPE: DNA
<213> ORGANISM: artificial sequence
<220> FEATURE:
<223> OTHER INFORMATION: Reverse primer for P21 promoter

<400> SEQUENCE: 12
ctgtctgcac cttcgctcct                                                    20
```